United States Patent
Deligianni et al.

(10) Patent No.: US 10,585,060 B2
(45) Date of Patent: Mar. 10, 2020

(54) ON-CHIP BIOSENSORS WITH NANOMETER SCALE GLASS-LIKE CARBON ELECTRODES AND IMPROVED ADHESIVE COUPLING

(71) Applicant: International Business Machines Corporation, Armonk, NY (US)

(72) Inventors: Hariklia Deligianni, Alpine, NJ (US); Bruce B. Doris, Hartsdale, NY (US); Damon B. Farmer, White Plains, NY (US); Steven J. Holmes, Ossining, NY (US); Qinghuang Lin, Yorktown Heights, NY (US); Nathan P. Marchack, New York, NY (US); Deborah A. Neumayer, Danbury, CT (US); Roy R. Yu, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 236 days.

(21) Appl. No.: 15/720,986

(22) Filed: Sep. 29, 2017

(65) Prior Publication Data

US 2019/0101503 A1      Apr. 4, 2019

(51) Int. Cl.
*G01N 27/327*     (2006.01)
*G01N 33/94*      (2006.01)
(Continued)

(52) U.S. Cl.
CPC ......... *G01N 27/3277* (2013.01); *G01N 27/48* (2013.01); *G01N 33/5438* (2013.01);
(Continued)

(58) Field of Classification Search
CPC ............... G01N 27/48; G01N 27/3277; G01N 27/3278; G01N 27/3273; G01N 27/4146;
(Continued)

(56) References Cited

U.S. PATENT DOCUMENTS

| 2005/0233555 A1* | 10/2005 | Rajagopalan ......... C23C 16/325 438/483 |
| 2012/0208283 A1* | 8/2012 | Gheorghiu ......... G01N 21/1717 436/94 |

(Continued)

FOREIGN PATENT DOCUMENTS

| CN | 104792843 A | 7/2015 |
| CN | 204649682 U | 9/2015 |

(Continued)

OTHER PUBLICATIONS

Deligianni et al., "On-Chip Biosensors With Nanometer Scale Glass-Like Carbon Electrodes and Improved Adhesive Coupling," U.S. Appl. No. 15/802,802, filed Nov. 3, 2017.
(Continued)

*Primary Examiner* — Gurpreet Kaur
(74) *Attorney, Agent, or Firm* — Cantor Colburn LLP; Vazken Alexanian

(57) ABSTRACT

Embodiments of the invention are directed to a biosensing integrated circuit (IC). A non-limiting example of the biosensing IC includes a plurality of semiconductor substrate layers. A sensor element is formed over a first one of the plurality of semiconductor substrate layers, wherein the sensor element is configured to, based at least in part on the sensor element interacting with a predetermined material, generate data representing a measureable electrical parameter. An adhesion enhancement region is configured to physically couple the sensor element to the first one of the plurality of semiconductor substrate layers. In some embodiments of the invention, the biosensing IC further includes an
(Continued)

electrically conductive interconnect network configured to communicatively couple the data representing the measureable electrical parameter to computer elements.

7 Claims, 23 Drawing Sheets

(51) Int. Cl.

| | | |
|---|---|---|
| *H01L 21/768* | (2006.01) | |
| *G01N 27/48* | (2006.01) | |
| *H01L 23/48* | (2006.01) | |
| *H01L 23/528* | (2006.01) | |
| *G01N 33/543* | (2006.01) | |
| *H01L 27/15* | (2006.01) | |
| *G01N 33/487* | (2006.01) | |

(52) U.S. Cl.
CPC .. *H01L 21/76877* (2013.01); *H01L 21/76898* (2013.01); *H01L 23/481* (2013.01); *H01L 23/528* (2013.01); *G01N 27/3278* (2013.01); *G01N 33/48728* (2013.01); *G01N 33/9413* (2013.01); *H01L 27/153* (2013.01)

(58) Field of Classification Search
CPC .......... G01N 27/4148; G01N 33/9413; G01N 33/48728; G01N 21/27; G01N 2223/304; G01N 2223/6113; H01L 21/76877; H01L 21/76898; H01L 23/481; H01L 23/528
See application file for complete search history.

(56) References Cited

U.S. PATENT DOCUMENTS

| | | | |
|---|---|---|---|
| 2012/0247978 A1* | 10/2012 | Zevenbergen | G01N 27/4045 205/787 |
| 2014/0024068 A1* | 1/2014 | Gratzl | G01N 33/5008 435/29 |
| 2016/0054659 A1 | 2/2016 | Shin et al. | |
| 2019/0041355 A1* | 2/2019 | Merriman | G01N 27/4146 |

FOREIGN PATENT DOCUMENTS

| | | |
|---|---|---|
| CN | 105758907 A | 7/2016 |
| DE | 3429768 A | 2/1986 |

OTHER PUBLICATIONS

List of IBM Patents or Patent Applications Treated as Related; Date Filed: Sep. 29, 2017, 2 pages.
Anonymous, "Glassy Carbon Product Information," Materials brochure from SPI Supplies, www.2SPI.com, Jul. 2016, 3 pages.
Dai et al., "Novel amperometric immunosensor for rapid separation-free immunoassay of carcinoembryonic antigen," Journal of Immunological Methods 287, 2004, pp. 13-20.
Garcia-Rodriguez et al., "Copper electrodeposition on glassy carbon and highly oriented pyrolytic graphite substrates from perchlorate solutions," Quimica Nova 35.4, 2012, pp. 699-704.
Kakhki, "A review to recent developments in modification of carbon fiber electrodes," Arabian Journal of Chemistry, 2014, 12 pages.
Moghadasi, "Investigation of adhesion layer for hybrid metal and glassy-carbon (GC) microelectromechanical systems (MEMS)," Doctoral dissertation, San Diego State University, 2016, 84 pages.
Robinson et al., "Monitoring Rapid Chemical Communication in the Brain," Chemical Reviews 108, 2008, pp. 2554-2584.
Schueller et al., "Fabrication of glassy carbon microstructures by soft lithography," Sensors and Actuators A: Physical 72.2, 1999, pp. 125-139.
Schwerdt et al., "Subcellular Probes for Neurochemical Recording from Multiple Brain Sites," Lab on a Chip 17.6, 2017, 19 pages.
Tiwari et al., "Surface Treatment of Carbon Fibers—A Review," Procedia Technology 14, 2014, pp. 505-512.
Vomero et al., "Highly Stable Glassy Carbon Interfaces for Long-Term Neural Stimulation and Low-Noise Recording of Brain Activity," Scientific Reports 7, 2017, 14 pages.
Yi et al., "3D carbon nanofiber microelectrode arrays fabricated by plasma-assisted pyrolysis to enhance sensitivity and stability of real-time dopamine detection," Biomedical Microdevices 18.6, 2016, 9 pages.

* cited by examiner

ON-CHIP BIOSENSORS WITH NANOMETER SCALE GLASS-LIKE CARBON ELECTRODES AND IMPROVED ADHESIVE COUPLING

BACKGROUND

The present invention relates in general to biosensors. More specifically, the present invention relates to fabrication methodologies and resulting structures for on-chip biosensors having nanometer scale glass-like carbon electrodes and improved adhesive and/or physical coupling to the chip substrate.

Electrochemistry studies the relationship between electricity and identifiable chemical or biochemical changes. For example, an ionic species of interest in a solution can be identified and measured by analyzing electric charges that move between biosensors in the solution and the various ionic species in the solution. A biosensor can be defined as an analytical device that converts a biological or bio/chemical response to an electric signal. An example biosensor configuration uses a compact analytical device such as an electrode to generate a measureable electrical parameter (e.g., current) based at least in part on detecting and/or measuring one or more analytes. The electrode may or may not incorporate a biological or biologically derived recognition element to enhance and/or target the electrode's detection sensitivity. Glass-like carbon, which is often referred to as glassy carbon or vitreous carbon, is considered an optimal material for forming the electrodes used in biosensors.

SUMMARY

Embodiments of the invention are directed to a biosensing integrated circuit (IC). A non-limiting example of the biosensing IC includes a plurality of semiconductor substrate layers. A sensor element is formed over a first one of the plurality of semiconductor substrate layers, wherein the sensor element is configured to, based at least in part on the sensor element interacting with a predetermined material, generate data representing a measureable electrical parameter. An adhesion enhancement region is configured to physically couple the sensor element to the first one of the plurality of semiconductor substrate layers. In some embodiments of the invention, the biosensing IC includes an electrically conductive interconnect network configured to communicatively couple the data representing the measureable electrical parameter to computer elements.

Embodiments of the invention are directed to a method of forming a biosensing IC. A non-limiting example of the method includes forming a plurality of semiconductor substrate layers, forming a sensor element over the first one of the plurality of semiconductor substrate layers, and configuring the sensor element to, based at least in part on the sensor element interacting with a predetermined material, generate data representing a measureable electrical parameter. The method further includes forming an adhesion enhancement region and configuring the adhesion enhancement region to physically couple the sensor element to the first one of the plurality of semiconductor substrate layers. In some embodiments of the invention, the method of forming the biosensing IC further includes forming an electrically conductive interconnect network and configuring the electrically conductive interconnect network to communicatively couple the data representing the measureable electrical parameter to computer elements.

Embodiments of the invention are directed to a method of using a biosensing IC. A non-limiting example of the method includes accessing a sample of fluid and exposing the sample of fluid to a sensor element of the biosensing IC. The biosensing IC includes a plurality of semiconductor substrate layers, as well as the sensor element being formed over a first one of the plurality of semiconductor substrate layers, wherein the sensor element is configured to, based at least in part on the sensor element interacting with a predetermined material, generate data representing a measureable electrical parameter. The biosensing IC further includes an adhesion enhancement region configured to physically couple the sensor element to the first one of the plurality of semiconductor substrate layers. In some embodiments of the invention, the biosensing IC further includes an electrically conductive interconnect network configured to communicatively couple the data representing the measureable electrical parameter to computer elements. The method further includes, based at least in part on the sensor element interacting with the predetermined material, using the sensor element to generate data representing the measureable electrical parameter.

Additional features and advantages are realized through the techniques described herein. Other embodiments and aspects are described in detail herein. For a better understanding, refer to the description and to the drawings.

BRIEF DESCRIPTION OF THE DRAWINGS

The subject matter which is regarded as the present invention is particularly pointed out and distinctly claimed in the claims at the conclusion of the specification. The foregoing and other features and advantages are apparent from the following detailed description taken in conjunction with the accompanying drawings in which:

DETAILED DESCRIPTION

Figure 1:
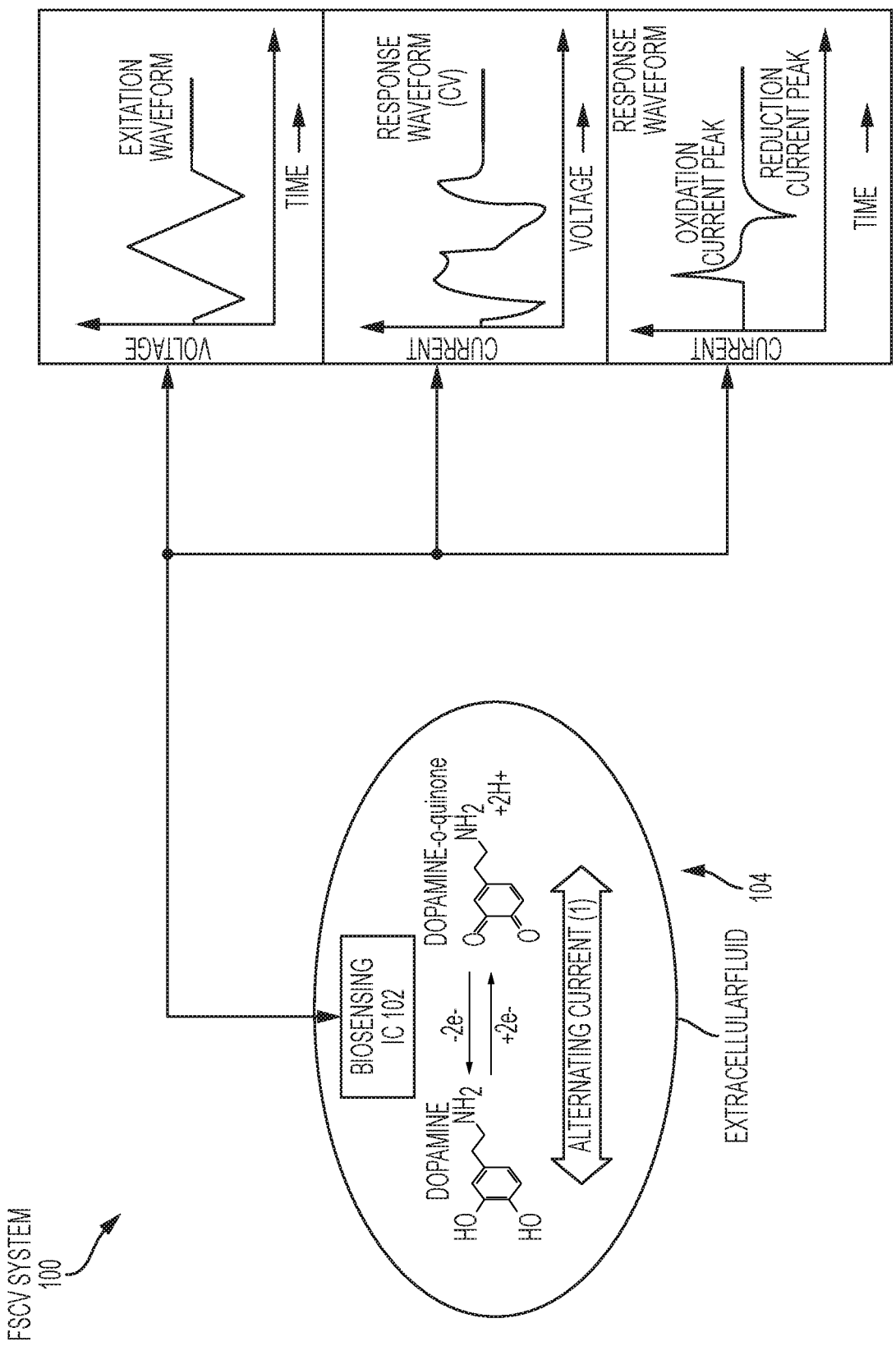
FIG. 1 depicts a diagram of a fast-scan cyclic voltammetry (FSCV) system incorporating an IC with a nanometer scale biosensor according to embodiments of the invention.

Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

Spatially relative terms, e.g., "beneath," "below," "lower," "above," "upper," and the like, are used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device can be otherwise oriented (e.g., rotated 90 degrees or at other orientations), and the spatially relative descriptors used herein should be interpreted accordingly.

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Turning now to an overview of technologies that are more specifically relevant to aspects of the present invention, biosensors are analytical tools that are useful for a variety of applications including medical diagnostics, drug discovery, treatments of diseases, food safety, agricultural and environmental monitoring, security, defense, and the like. There are many different types of biosensors, which are typically categorized based on the biosensor's biological recognition elements and transducer elements. For example, an example biosensor configuration includes a biological sensitive recognition element (e.g., antibodies, nucleic acids, enzymes, or aptamers) immobilized on a physicochemical transducer and connected to a detector to identify the presence, concentrations and/or kinetics of one or more specific analytes in a sample. In biosensors formed from glass-like carbon electrodes, the glass-like carbon electrode can function as both the recognition element and the transducer. The specificity and selectivity of the biosensor is determined by the catalytic or affinity properties of the biological recognition element. The signal originating from the interaction between the analyte of interest and the biological recognition element is then transformed by a transducer to an optical or electrical readout. Biosensors are consider to be more reliable, accurate, cost effective, and easy to use compared to other conventional lab-based detection techniques due to their portability, reusability, real-time response, and high specificity, sensitivity and selectivity.

Fast-scan cyclic voltammetry (FSCV) is a biosensing technique that was developed in the early 1980s. FSCV is based on cyclic voltammetry, which is a classic electrochemical technique that offers high chemical resolving power. FSCV accelerates classic cyclic voltammetry techniques by several orders of magnitude to provide temporal resolution on a sub-second time scale (typically 100 ms). The most common substrate for analyte detection is a carbon surface (usually a carbon-fiber microelectrode), which offers a relatively broad voltage range in aqueous solutions.

Using FSCV with carbon-fiber microelectrodes, changes in the extracellular concentration of electro-active molecules can be monitored. One such molecule that is of biological interest is the neurotransmitter dopamine. Using FSCV, the potential at the microelectrode is ramped back and forth between a potential that is insufficient to oxidize dopamine and an oxidizing potential at a high scan rate (e.g., 400 V/s) multiple times each second. When dopamine is present in the solution at the surface of the electrode, it is oxidized during the positive sweep to form dopamine-o-quinone, and is reduced back to dopamine in the negative sweep. During the negative sweep (i.e., the redux phase), electrons are transferred between these molecules and the microelectrode (electrolysis). This flux of electrons is measured as a current that is directly proportional to the number of molecules that undergo electro-oxidation. For analyte identification, current during a voltammetric scan can be plotted against the applied potential to yield a cyclic voltammogram. The cyclic voltammogram provides chemical information that is fairly unique for each substance, which allows resolution of dopamine from other electro-active compounds. For quantification of changes in dopamine concentration over time, the current at its peak oxidation potential can be plotted for subsequent voltammetric scans. This approach can be utilized to make rapid chemical measurements in a range of biological preparations and conditions. FSCV can be used to record dopamine in real time, in awake rodents engaging in a variety of behavioral tasks. Although carbon fiber microelectrodes can be used to make in vivo FSCV measurements, they are still relatively large (e.g., 7 microns in diameter, 100 microns in length), which compromises the ability to make more granular observations and measurements.

Glass-like carbon, which is often referred to as glassy carbon or vitreous carbon, is considered an optimal material for forming the electrodes used in biosensing systems, particularly in FSCV systems. Glass-like carbon is a non-graphitizing carbon that combines glassy and ceramic properties with those of graphite. The useful properties of glass-like carbon in biosensor applications can include high temperature resistance, hardness (e.g., 7 Mohs), low density, low electrical resistance, low friction, low thermal resistance, extreme resistance to chemical attack and impermeability to gases and liquids.

It is a challenge to provide biosensors that include glass-like carbon electrodes, nanometer scale dimensions for sensing at a more granular level (e.g., across the height and/or width of an individual neuron), and good adhesion to a substrate carrier (e.g., a semiconductor wafer/chip).

Turning now to an overview of aspects of the present invention, embodiments of the invention provide fabrication methodologies and resulting structures for on-chip nanometer scale biosensors having glass-like carbon electrodes and improved adhesive and/or physical coupling to the chip substrate. In embodiments of the invention, nanometer scale dimensions can be achieved by using known semiconductor fabrication processes (e.g., spin coating, chemical vapor deposition, lithographic patterning, etching, etc.) to deposit a layer of a glass-like carbon precursor (e.g., a carbon-rich polymer applied as an organic planarization layer (OPL)) on a substrate carrier, and then applying a high temperature anneal (e.g., about 900 Celsius degrees to about 1200 Celsius degrees) to convert the glass-like carbon precursor to a layer of glass-like carbon material. The layer of glass-like carbon material can be patterned and etched to form one or more pillars. In embodiments of the invention, the pillars are high aspect ratio structures each having a height less than ten (10) microns and a width less than one (1) micron in diameter. Forming the electrode as high aspect ratio pillars provide additional detection surface area, which improves detection efficiency, signal strength, and signal to noise ratios. Forming the glass-like electrodes at nanometer scale dimensions using known semiconductor device fabrication techniques enables sensing measurements to be made at a highly granular level (e.g., across the height and/or width of an individual neuron).

Embodiments of the invention provide a substantially self-contained nanometer scale biosensing system by forming the nanometer scale glassy electrode, along with an arrangement of electrical components (e.g., computing elements, LEDs, power supplies, wireless transmitters/receivers, etc.), in an IC. To improve adhesion between the post-annealed glass-like carbon material and the IC substrate, embodiments of the invention provide an enhanced adhesive/physical coupling region configured and arranged to physically couple the post-annealed glass-like carbon material and the IC substrate.

In embodiments of the invention, the enhanced adhesive/physical coupling region can be implemented as intervening layer of material selected to have good adhesive/physical coupling the post-annealed glass-like carbon material, as well as good adhesive/physical coupling to the IC substrate. In embodiments of the invention, the enhanced adhesive/physical coupling region can include a silicon carbide material. In embodiments of the invention, the enhanced adhesive/physical coupling region can include a plasma carbon material. In embodiments of the invention, the enhance adhesive/physical coupling region can be implemented by providing topologies on the enhanced adhesive/physical coupling region and the IC substrate that can physically mate. For example, a groove or notch can be formed in or on IC substrate and a corresponding protrusion can be formed in or on the nanometer scale glass-like carbon electrodes. During fabrication, the protrusion is mated inside the groove, which in effect physically locks the enhanced adhesive/physical coupling region and IC substrate in place. The mated protrusion/groove can prevent post-high-temperature-anneal shrinkage in the enhanced adhesive/physical coupling region and/or the glass-like carbon electrodes from delaminating the enhanced adhesive/physical coupling region and/or the glass-like carbon electrodes from the IC substrate.

To avoid having the high temperature anneal damage the arrangement of electrical components (e.g., computing elements, LEDs, power supplies, wireless transmitters/receivers, etc.), biosensing IC is implemented as a multi-substrate IC, and the glass-like carbon electrodes are formed a on a different substrate from the arrangement of electrical components.

In embodiments of the invention, the self-contained nanometer scale biosensor IC include an interconnect network that enables selective, localized access to electrodes within the array of electrodes.

Accordingly, embodiments of the invention provide on-chip biosensors that include glass-like carbon electrodes, nanometer scale dimensions for sensing at a more granular level (e.g., across the height and/or width of an individual neuron), and good adhesion to a substrate carrier (e.g., a semiconductor wafer/chip).

Turning now to a more detailed description of aspects of the present invention, FIG. 1 depicts a diagram of a FSCV system 100 that incorporates a biosensing IC 102 having an on-chip nanometer scale biosensor system with improved adhesive and/or physical coupling to the chip substrate according to embodiments of the invention. Although embodiments of the invention are described herein in connection with a FSCV biosensing methodology and system, the techniques of the present invention are applicable to a variety of different types of biosensing methodologies and systems. The novel fabrication methodologies and resulting structures illustrated and described herein allow the electrode portions of the sensing elements of the biosensing IC 102 to be formed at nanometer scale dimensions from glass-like carbon, and with an adhesion enhancement region that improves the adhesive (or physical) coupling of the glass-like carbon electrode to the semiconductor substrate of the biosensing IC 102. Additional details of fabrication methodologies and resulting structures for the biosensing IC 102 are illustrated and described in the accompanying figures and subsequent paragraphs herein.

According to embodiments of the invention, the biosensing IC 102 can include a plurality of semiconductor substrate layers. A sensor element is formed over a first one of the plurality of semiconductor substrate layers. The sensor element is configured to, based at least in part on the sensor element interacting with a predetermined material, generate data representing a measureable electrical parameter. An adhesion enhancement region is configured to physically couple the sensor element to the first one of the plurality of semiconductor substrate layers. In some embodiments of the invention, the biosensing IC 102 includes an electrically conductive interconnect network configured to communicatively couple the data representing the measureable electrical parameter to computer elements.

In the example depicted in FIG. 1, the FSCV system 100 is used to measure changing concentrations of dopamine in extracellular fluid 104. The FSCV system 100 incorporates the biosensing IC 102 of the present invention, which can be inserted, for example, into the extracellular fluid 104, a living cell or tissue. The glass-like carbon electrodes of the biosensing IC 102 are nanometer scale and can be arranged in a variety of configurations suitable for performing FSCV. In an example configuration, three types of glass-like carbon electrodes can be provided, and each such electrode configured to perform a different function in the FSCV process. The first type of glass-like carbon electrode is the working electrode, which is also known as the test or indicating electrode. The electrochemical phenomena (e.g., reduction and/or oxidation) being investigated takes place at the working electrode. The second type of glass-like carbon electrode is the reference electrode. The voltage potential of the working electrode is constant enough that it is used as the reference standard against which the potentials of the other two electrodes can be measured. The third type of glass-like carbon electrode is the counter or auxiliary electrode, which serves as a source or sink for electrons so that current can be passed from current-generating on-chip computing elements of the biosensing IC 102 to the extracellular fluid 104.

Using the above-described three-electrode FSCV configuration, a nanometer scale auxiliary electrode of the biosensing IC 102 is stimulated by applying a quickly changing voltage in a triangular wave fashion, which is illustrated by excitation waveform 106. High resolution can be achieved by changing the voltage at very high speeds, referred to as a fast scan rate. When the voltage in the extracellular fluid 104 is in the correct range (e.g., ±1 Volt), dopamine is repeatedly oxidized and dopamine-O-quinone is repeatedly reduced. Using sub-second scan rates can result in compounds being oxidized and reduced in microseconds. The repeated oxidation and reduction results in a movement of electrons in the extracellular fluid 104 that will ultimately create a small alternating current (e.g., nano amps scale), which can be sensed and measured by a nanometer scale glass-like carbon working electrode of the biosensing IC 102. Processor portions of the on-chip computing elements of the biosensing IC 102 receive and process the alternating current. By processing the input and output currents, the on-chip computing elements of the biosensing IC 102 can generate a voltage vs. current plot (e.g., response CV waveform 108) that is unique to each compound under investigation. Because the time scale of the voltage oscillations is known, this can then be used to calculate a plot of the current in the extracellular fluid 104 as a function of time (e.g., response waveform 110). The relative concentrations of dopamine can be calculated as long as the number of electrons transferred in each oxidation and reduction reaction is known.

Because aspects of the invention allow the biosensing IC 102 to include glass-like carbon electrodes formed at nanometer scale dimensions (e.g., each electrode pillar can be less than about one (1) micron in width and less than about ten (10) microns in height) with good adhesive/physical coupling to the substrate of the biosensing IC 102, the biosensing IC 102 is small enough to scan across an individual neuron (e.g., about 100 microns in width) and map out the behavior of the individual neuron. These and other aspects of the invention enable beneficial measurements techniques (e.g., FSCV) and glass-like carbon electrodes to be applied at a more granular level. For example, the improved functional granularity and other features provided by aspects of the present invention enhance the chemical specificity and high resolution of FSCV techniques, which further improve the ability to use FSCV techniques to detect changing chemical concentrations in vivo. The chemical specificity of FSCV is derived from reduction potentials. Every compound has a unique reduction potential, and so the alternating voltage can be set to select for a particular compound. As a result of the improved functional granularity and other feature provided by aspects of the invention, the granularity and precision of FSCV techniques used to measure a variety of electrically active biological compounds such as catacholamines, indolamines, and neurotransmitters is enhanced. The granularity of detected concentration changes in ascorbic acid, oxygen, nitric oxide, and hydrogen ions (pH) can also be enhanced by the above-described aspects and/or features of the present invention. Aspects of the present invention further enhance the ability to use FSCV techniques to measure multiple compounds at the same time. The nanometer scale glass-like electrodes of the present invention can be noninvasively inserted into live tissues. The nanometer scale size of the described electrodes also permits the biosensing IC 102 to probe very specific and very granular brain regions, including, for example, across an individual neuron having, for example, a width of about 100 microns. Thus, aspects of the invention improve the ability of biosensing techniques such as FSCV to measure chemical fluctuations of living organisms and can be used to in enhance a variety of neurotransmitter-based procedures such as the control/influence of electrophysiological and opto-genetic functionality, mapping of neural action, intervention in neural processes affecting behavior, and generating devices and procedures for therapy of motivation disorders such as addition, depression, and schizophrenia.

Figure 2:
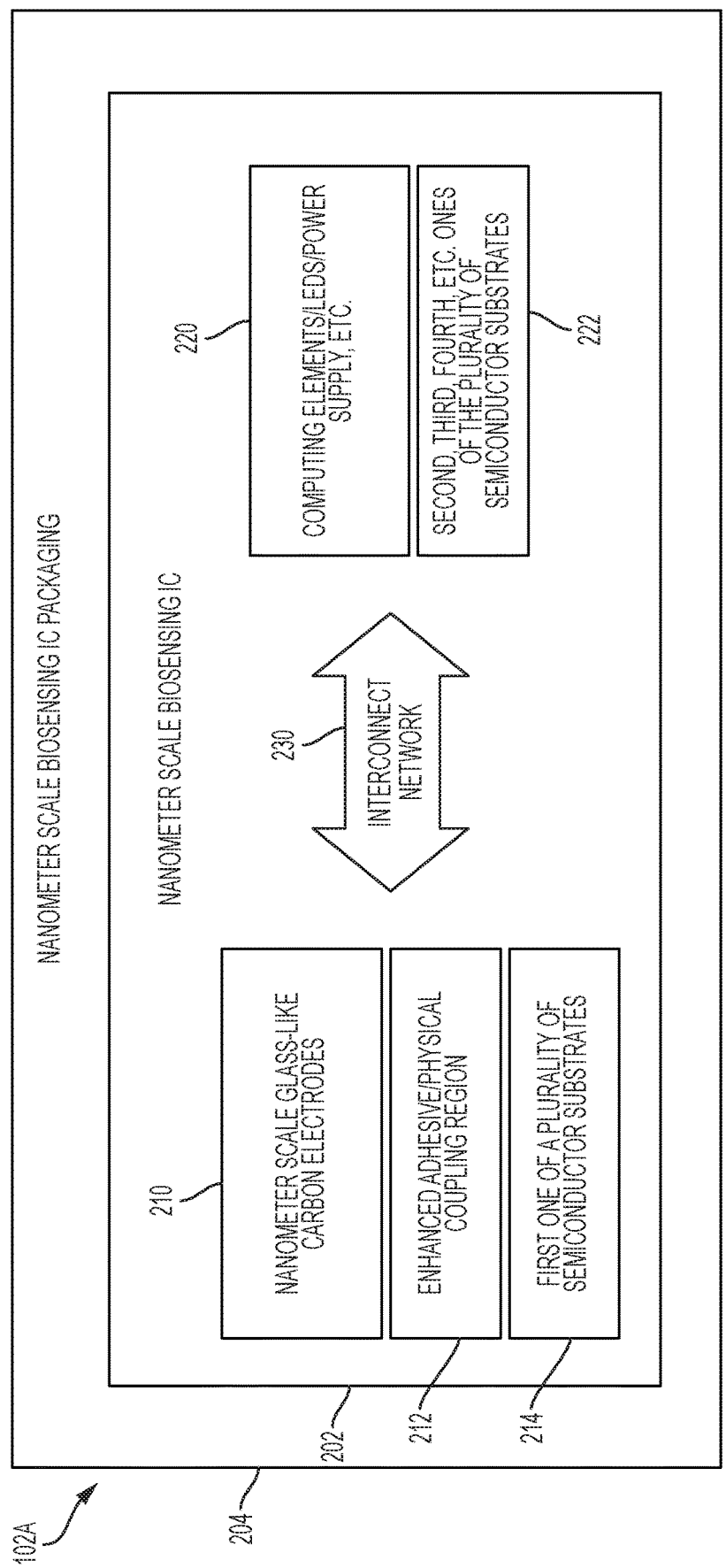
FIG. 2 depicts a block diagram illustrating a more detailed example of an IC with a nanometer scale biosensor according to embodiments of the invention.

FIG. 2 depicts a block diagram illustrating a biosensing IC 102A having an on-chip nanometer scale biosensor system 202 with improved substrate adhesion according to embodiments of the invention. The biosensing IC 102A shown in FIG. 2 is a more detailed example of the biosensing IC 102 shown in FIG. 1. The biosensor 102A includes the on-chip nanometer scale biosensor system 202, one or more nanometer scale glass-like carbon electrodes 210, an enhanced adhesive/physical coupling region 212, a first one of a plurality of semiconductor substrates 214, an arrangement of electrical components (e.g., computing elements, LEDs, power supplies, etc) 220, a second (or third, fourth, etc.) one of the plurality of semiconductor substrates 222, an electrically conductive interconnect network 230, and biosensing IC packaging 204, configured and arranged as shown.

The thicknesses of the respective layers of the novel biosensing IC 102A described herein can vary according to design considerations. For example, the thicknesses of the layers of the novel biosensing IC 102A can be designed to have predetermined thicknesses, to have thicknesses within predetermined ranges, to have thicknesses having fixed ratios with respect to each other, or to have thicknesses based on any other consideration or combination of considerations in accordance with the various functionalities described herein.

The nanometer scale glass-like carbon electrodes 210 can be configured in a variety of arrangements based on the particular electrochemical analysis to which the nanometer scale glass-like carbon electrodes 210 will be applied. In embodiments of the invention that utilize the nanometer scale glass-like carbon electrodes 210 to perform FSCV operations, the nanometer scale glass-like carbon electrodes 210 can be configured to include, for example, the three types of glass-like carbon electrodes previously described in connection with the biosensing IC 102 show in FIG. 1, namely a working electrode, a reference electrode, and an auxiliary electrode.

According to embodiments of the invention, the methodology for fabricating the glass-like carbon material of the nanometer scale glass-like carbon electrodes 210 is incorporated into the process for fabricating the overall biosensing IC 102A. In other words, the glass-like material of the nanometer scale glass-like carbon electrodes 210 is not pre-fabricated. Instead, according to embodiments of the invention, a precursor to glass-like carbon material is deposited over the first one of the plurality of semiconductor substrates 214, and then the precursor is processed to convert the precursor to a glass-like carbon material. In embodiments of the invention, the precursor material can be a phenol polymer, and the processing to convert the precursor to glass-like carbon includes exposing the precursor phenol polymer to a high temperature anneal (e.g., above about 900 Celsius degrees) for a sufficient time to effect the conversion to a material having the desired properties of glass-like carbon. In embodiments of the invention, the precursor phenol polymer can be implemented as an organic planarization layer (OPL). The OPL can be a self-planarizing organic material such as a polymer with sufficiently low viscosity that the top surface of the applied polymer forms a planar horizontal surface. Non-limiting examples of suitable OPL materials include, but are not limited to, materials available from JSR Corporation under the tradenames HM8006 and HM8102. The OPL can be applied, for example, by spin-coating. In embodiments of the invention, the thickness of the OPL can be from about 100 nm to about 10 microns, although lesser and greater thicknesses can also be employed.

According to embodiments of the invention, the post-anneal glass-like carbon material can be formed into one or more nanometer scale pillars (e.g., pillars 1302 shown in FIG. 13) using pattern etching material processing methodologies. Pattern etching involves the application of a thin layer of light-sensitive material, such as photo-resist, to an upper surface of a substrate material (e.g., the post-anneal glass-like carbon) that is subsequently patterned in order to provide a mask for transferring this pattern to the underlying thin layer of light sensitive material on the substrate during etching. The patterning of the light-sensitive material generally involves exposure by a radiation source through a reticle (and associated optics) of the light-sensitive material using, for example, a photo-lithography system, followed by the removal of the irradiated regions of the light-sensitive material (as in the case of positive photo-resist), or non-irradiated regions (as in the case of negative resist) using a developing solvent.

In embodiments of the invention, the mask layer can include multiple sub-layers. By utilizing a multi-layer mask, the top mask layer, which includes the light-sensitive material as described above, can be thinner and, therefore, a smaller feature size (e.g., nanometer scale features sizes) can be achieved using conventional photo-lithography techniques. In order to generate a mask layer of sufficient thickness for the ensuing primary etch process, additional material layers can be formed underlying the top mask layer. The pattern, formed in the top mask layer using lithographic techniques, is transferred to the underlying layer or layers that include the mask layer for the primary etch process.

Embodiments of the invention form the arrangement of electrical components (e.g., computing elements, LEDs, power supplies, etc) 220 in a manner that does not expose the electrical components 220 to the above-described high temperature anneal (e.g., above about 900 Celsius degrees), thereby avoiding the high temperature anneal having a negative impact on the arrangement of electrical components 220. According to some embodiments of the invention, high-heat-related negative impact to the electrical components 220 can be avoided by segregating the electrical components 220 to a different region of the semiconductor substrate than the semiconductor substrate region in which the nanometer scale glass-like carbon electrodes 210 is located, as well as by forming the electrical components 220 subsequently to the application of the high temperature anneal.

In some embodiments of the invention, the high-heat-related negative impact to the electrical components 220 is avoided by forming the biosensing IC 102A as multi-substrate (or multi-layer), three-dimensional (3D) IC, and by floor planning the 3D ICs such that the electrical components 220 are formed on a different semiconductor substrate than the semiconductor substrate on which the nanometer scale glass-like carbon electrodes 210. Accordingly, in embodiments of the invention, the biosensing IC 102A can be a stacked substrate IC in a so-called 3D format. A 3D semiconductor device (or stacked substrate IC) can contain two or more semiconductor substrates stacked vertically so they occupy less space than two or more conventionally arranged semiconductor substrates. The stacked substrate IC can be built by stacking the substrates and/or ICs and interconnecting them vertically so that they behave as a single IC. The stacked substrates of the stacked substrate IC can be wired together using input/output ports either at the perimeter of the stacked IC or across the area of the stacked IC or both. Through-silicon vias (TSVs) can be used to completely or partly replace edge wiring by creating vertical connections through the semiconductor substrates. By using TSV technology, stacked substrate IC devices can pack a great deal of functionality into a small footprint.

The above-described high temperature anneal can cause volume shrinkage (e.g., from about 30% to about 50%) in the resulting glass-like carbon material, which can result in some delamination of the glass-like carbon electrodes 210, and can also have a negative impact on the adhesive or physical coupling between the nanometer scale glass-like carbon electrodes 210 and the first one of the plurality of semiconductor substrates 214. The enhanced adhesive/physical coupling region 212 according to embodiments of the invention is provided to avoid the above-described high temperature anneal having a negative impact on the adhesive or physical coupling between the nanometer scale glass-like carbon electrodes 210 and the first one of the plurality of semiconductor substrates 214. The enhanced adhesive/physical coupling region 212, according to embodiments of the invention, is configured and arranged in a manner that improves the adhesive/physical coupling between the nanometer scale glass-like carbon electrodes 210 and the first one of the plurality of semiconductor substrates 214.

For example, in embodiments of the invention, the enhanced adhesive/physical coupling region 212 includes a material having good adhesive/physical coupling to the glass-like carbon electrodes 210, along with a material having good adhesive/physical coupling to the first one of the plurality of semiconductor substrates 214. For example, where the first one of the plurality of semiconductor substrates 214 includes silicon, the enhanced adhesive/physical coupling region 212 could be formed, according to embodiments of the invention from a silicon carbide on material. The silicon component of the enhanced adhesive/physical coupling region 212 provides good adhesive/physical coupling of the enhanced adhesive/physical coupling region 212 to the silicon first one of the plurality of semiconductor substrates 214. Similarly, the carbon component of the enhanced adhesive/physical coupling region 212 provides good adhesive/physical coupling of the enhanced adhesive/physical coupling region 212 to the glass-like carbon electrodes 210.

In some embodiments of the invention, the enhanced adhesive/physical coupling region 212 includes a carbon-rich polymer that is deposited on the first one of the plurality of semiconductor substrates 214 using a chemical vapor deposition (CVD) process. In some embodiments, the CVD process can be a plasma-enhanced CVD (PECVD) process that deposits thin films from a gas state (e.g., a carbon-rich gas species such as methane, ethylene, benzene, and the like) to a solid state (e.g., a carbon-rich polymer) on a substrate (e.g., the first one of the plurality of semiconductor substrates 214). Chemical reactions are involved in the PECVD process, which occur after creation of a plasma of the reacting gases. A plasma is any gas in which a significant percentage of the atoms or molecules are ionized. The plasma can be created by radio frequency (RF) or direct current (DC) discharge between two electrodes, the space between which is filled with the reacting gases.

Forming the enhanced adhesive/physical coupling region 212 from the PECVD-deposited carbon-rich polymer provides two useful adhesion and/or physical coupling related characteristics. Specifically, when it is exposed to the above-described high temperatures anneal, the PECVD-deposited carbon-rich polymer will not experience as much volume shrinkage as the phenol polymer OPL that acts as the pre-anneal precursor to the glass-like carbon material. For example, the high temperatures anneal can result in from about 30% to about 50% volume shrinkage in the pre-anneal phenol polymer OPL, and it is this volume shrinkage that would contribute to a post-anneal glass-like polymer delaminating from a direct adhesive/physical coupling to a semiconductor substrate. However, the high temperatures anneal can result in a lower percentage of post-anneal volume shrinkage in the range from about 20% to about 30% in the PECVD-deposited carbon-rich polymer. Having a lower percentage of post-anneal volume shrinkage means that forming the enhanced adhesive/physical coupling region 212 to include the PECVD-deposited carbon-rich polymer will result in less delamination of the PECVD-deposited carbon-rich polymer from the first one of the plurality of semiconductor substrates 214.

The second useful adhesion and/or physical coupling characteristic of the PECVD-deposited carbon-rich polymer is that it is carbon-rich (e.g., between about 80% and about 100% carbon). During the high temperatures anneal, the carbon in the PECVD-deposited carbon-rich polymer chemically binds with the carbon in the post-anneal glass-like carbon electrodes 210, which enhances the adhesion and/or physical coupling between the enhanced adhesive/physical coupling region 210 and the post-anneal glass-like carbon electrodes 210.

The enhanced adhesive/physical coupling region 212, according to embodiments of the invention, can be configured and arranged to improve the adhesive/physical coupling between the nanometer scale glass-like carbon electrodes 210 and the first one of the plurality of semiconductor substrates 214 by providing topologies on the enhanced adhesive/physical coupling region 212 and the first one of the plurality of semiconductor substrates 214 that can physically mate. For example, a groove or notch can be formed in or on the first one of the plurality of semiconductor substrates 214, and a corresponding protrusion can be formed in or on the enhanced adhesive physical coupling region 212. The corresponding groove can also be formed in or on the nanometer scale glass-like carbon material that forms the electrodes 210. During fabrication, the protrusion is mated inside the groove, which in effect physically locks the enhanced adhesive/physical coupling region 212 (or the nanometer scale glass-like carbon material that forms the electrodes 210) and the first one of the plurality of semiconductor substrates 214 and prevents shrinkage in the enhanced adhesive/physical coupling region 212, the nanometer scale glass-like carbon electrodes 210, or the glass-like carbon electrodes 210 from delaminating from the first one of the plurality of semiconductor substrates 214.

The above described example implementations of the enhanced adhesive/physical coupling region 212 are not mutually exclusive and can be utilized alone or in any combination with the other approaches. For example, the enhanced adhesive/physical coupling region 212 can be formed from the PECVD-deposited carbon-rich polymer and can include the above-described physically mating topologies.

The interconnect network 230 includes conductive interconnect layers that form a network of pathways that transport signals throughout an IC, thereby connecting circuit components of the IC into a functioning whole and to the outside world. Interconnect layers are themselves interconnected by a network of contact points formed through the wafers of the IC. For example, a through-silicon via (TSV) is an electrical contact point that passes completely through the semiconductor wafer or die. In multilevel IC configurations, for example, a TSV can be used to form vertical interconnections between a semiconductor device located on one level/substrate of the IC and an interconnect layer located on another level/substrate of the IC.

In its simplest configuration, a TSV is formed by creating a via (i.e., a hole or an opening) through the semiconductor wafer at a desired location, and then filling the via with conductive material, thereby providing a solid metal contact that extends from a front side of the wafer to a back side of the wafer. There are several considerations in forming TSVs, including but not limited to the purity and conductance of the TSV conductive material, ensuring that the via is planar with the front and back surfaces of the wafer, and the impact of the via aspect-ratio on the fabrication methodology used to form the via opening and the conductive material via fill.

The biosensing IC package 204 provides housing for the biosensing IC 202. After completion of device level and interconnect level fabrication processes, the semiconductor devices on the wafer are separated into micro-chips (i.e., chips), and the final products is packaged. IC packaging typically involves encasing the silicon chip(s) inside a hermetically sealed plastic, metal or ceramic package that prevents the chip(s) from being damaged by exposure to dust, moisture or contact with other objects.

Figure 3:
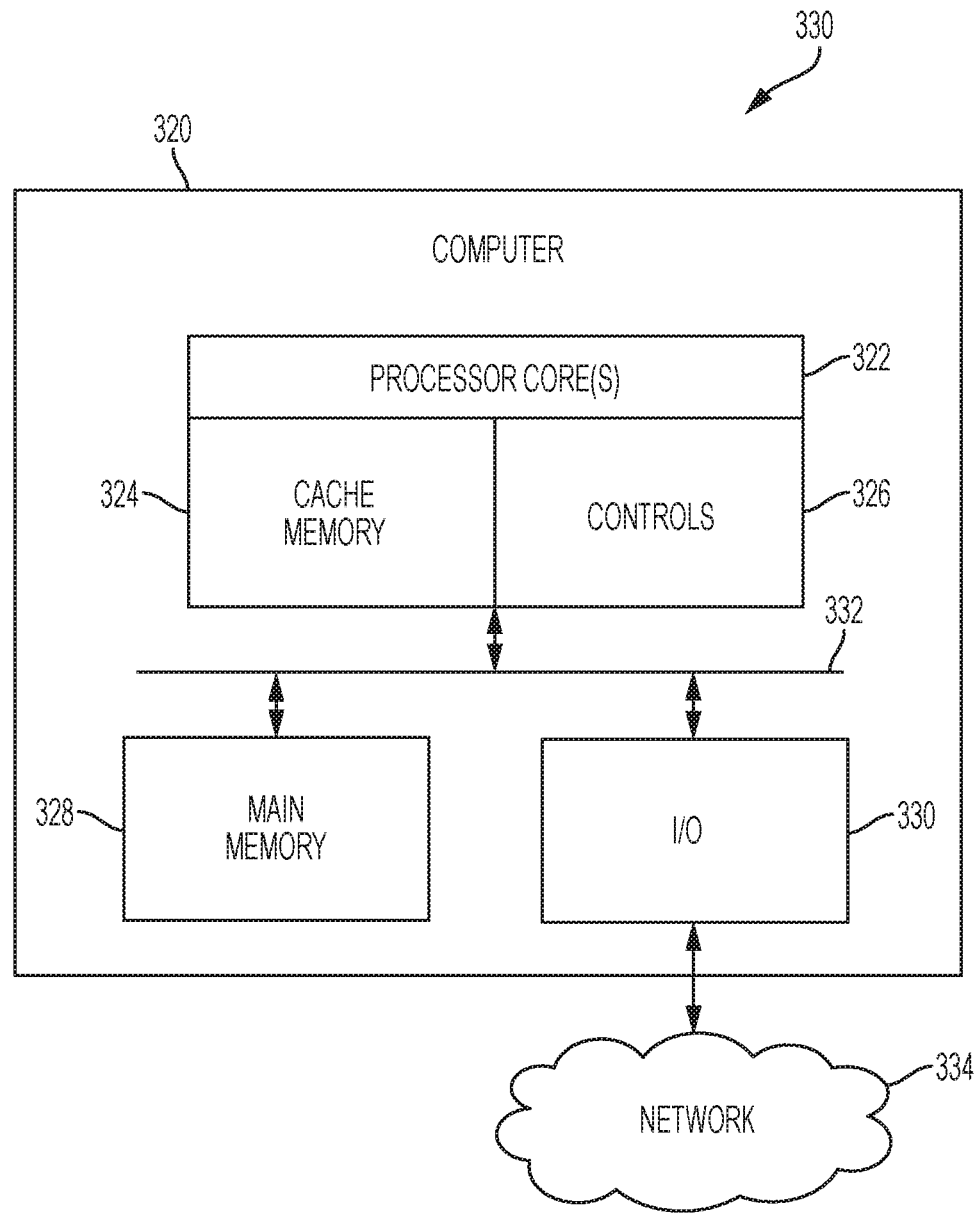
FIG. 3 depicts a block diagram showing additional details of a computer processor, which is an example of the arrangement of electrical components (e.g., computing elements, LEDs, power supplies, etc) shown in FIG. 2.

The arrangement of electrical components 220 shown in FIG. 2 can include computer processing elements, an example of which is depicted as a computer system 330 shown in FIG. 3. Computer system 330 includes an exemplary computing device ("computer") 320 configured to stimulate and receive outputs from the glass-like carbon electrodes 210 (shown in FIG. 2). The computer system 330 can also process/analyze the outputs of the glass-like carbon electrodes 210 in accordance with aspects of the present invention. In addition to computer 320, exemplary computer system 330 includes network 334, which connects computer 320 to additional systems (not depicted) and can include one or more wide area networks (WANs) and/or local area networks (LANs) such as the Internet, intranet(s), and/or wireless communication network(s). Computer 320 and additional systems are in communication via network 334, e.g., to communicate data between them.

Exemplary computer 320 includes processor cores 322, main memory ("memory") 328, and input/output component(s) 330, which are in communication via bus 332. Processor cores 322 include cache memory ("cache") 324 and controls 326. Cache 324 can include multiple cache levels (not depicted) that are on or off-chip from processor 322. Memory 324 can include various data stored therein, e.g., instructions, software, routines, etc., which, e.g., can be transferred to/from cache 324 by controls 326 for execution by processor 322. Input/output component(s) 330 can include one or more components that facilitate local and/or remote input/output operations to/from computer 320, such as a display, keyboard, modem, network adapter, etc. (not depicted).

Figure 4:
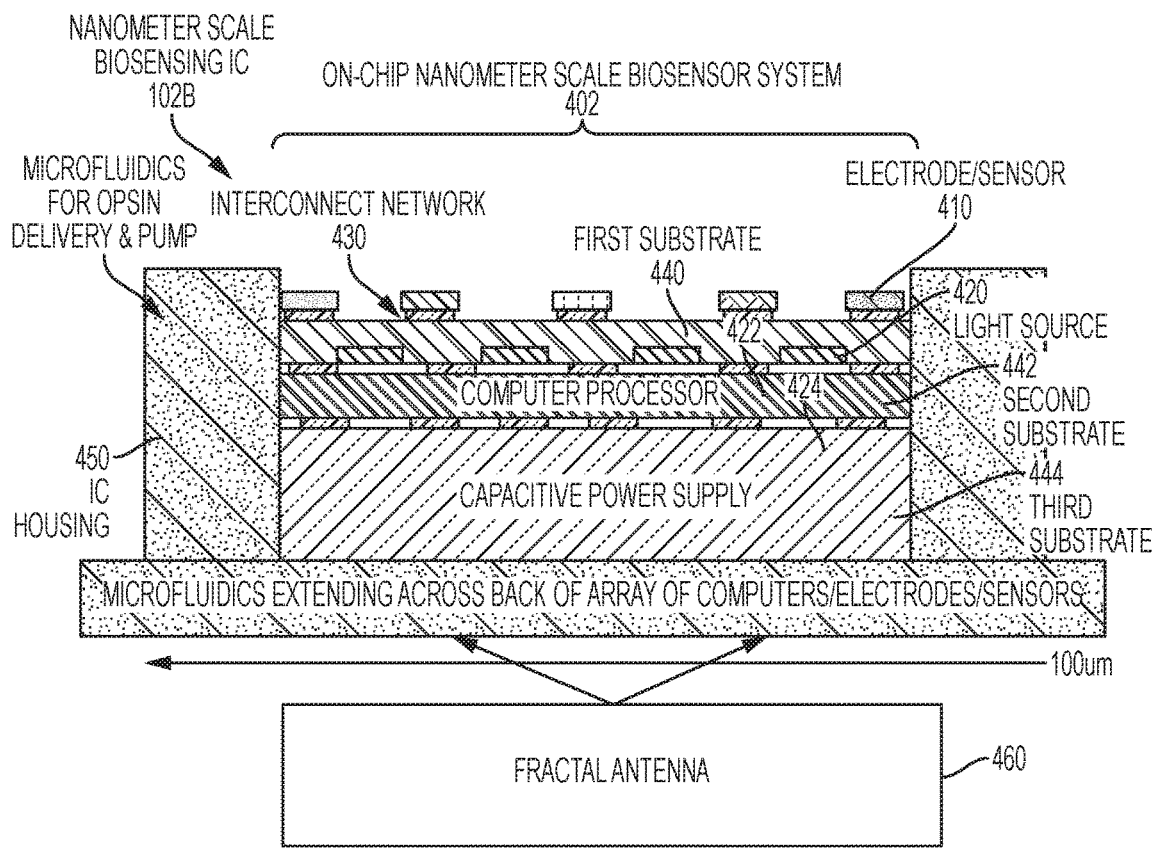
FIG. 4 depicts a schematic diagram of an IC with a nanometer scale biosensor according to embodiments of the invention.

FIG. 4 depicts a block diagram illustrating a biosensing IC 102B having an on-chip nanometer scale biosensor system 402 with improved substrate adhesion according to embodiments of the invention. The biosensing IC 102B shown in FIG. 4 is a more specific example of the biosensing IC 102A shown in FIG. 2 and the biosensing IC 102 shown in FIG. 1. The on-chip nanometer scale biosensor system 402 includes an array of nanometer scale glass-like carbon electrodes/sensors 410, an array of light sources 420 (e.g., light emitting diodes (LEDs)), computer processor elements 422, a capacitive power supply 424, a first substrate 440, a second substrate 442, a third substrate 444, an IC housing 450, and a fractal antenna 460, configured and arranged as shown.

In some embodiments of the invention, the light sources 420 can be formed on the first substrate 440, and the first substrate 440 can be a transparent dielectric (e.g., $SiO_2$) to facilitate passing light through the first substrate 440 to and from the light sources 420 in order to perform optical-based measurements such as optogenetic measurements. To avoid potentially negative impact from the high temperature anneal, the light sources 420 can be formed on the first substrate 440 subsequently to the high temperature anneal. In some embodiments of the invention, the light sources 420 can be formed on a substrate of the IC 102B other than the first substrate 440, including its own dedicated substrate in the IC 102B. In embodiments of the invention, the various methodologies for coupling the sensors/electrodes 410 to a substrate of the biosensing IC 102, 102A, 102B can also be used to couple the light sources 420 to a substrate of the biosensing IC 102, 102A, 102B. Multi-chip bonding can be used to attach and electrically couple the sensor/electrode substrate to the light source substrate. No matter the substrate to which the light sources 420 are attached, a pathway for light transmission to/from the light sources 420 is provided for the optoenetics measurements, either by making certain substrates optically transparent, or by providing openings in certain substrates.

Optogenetics is a technique that uses light to modulate membrane voltage in cells, such as neural cells, in body tissue. The light can be used to trigger changes in proteins that modulate membrane potentials in the cells through excitatory or inhibitory membrane currents. This ability to modulate cells has proven instrumental in preclinical studies and holds significant potential for the treatment of diseases such as Parkinson's, epilepsy, chronic pain, addiction, and depression, among others.

In embodiments of the invention, the IC housing 450 is formed from bio-compatible material to facilitate in vivo testing using the biosensing IC 102B. The IC housing can also include a network of microfluidic channels (not shown) for opsin pumping/delivery, which is used in optogenetics testing. In some embodiments of the invention, the IC 102B can be used ex vivo, and a probe or similar device can be used to withdraw fluid and provide it to the IC 102B.

The interconnect network 430 include conductive interconnect layers that form a network of pathways that transport signals throughout the IC 102B, thereby connecting circuit components of the IC 102B into a functioning whole and to the outside world. Interconnect layers are themselves interconnected by a network of contact points formed through the wafers of the IC. For example, a through-silicon via (TSV) is an electrical contact point that passes completely through the semiconductor wafer or die. In the multilevel configuration of IC 102B, for example, a TSV can be used to form vertical interconnections between a device located on one level/substrate of the IC 102B and an interconnect layer located on another level/substrate of the IC 102B.

The fractal antenna 460 can be used to provide wireless communications into and out of the IC 102B. A fractal antenna is an antenna that uses a fractal, self-similar design to maximize the length, or increase the perimeter (on inside sections or the outer structure), of material that can receive or transmit electromagnetic radiation within a given total surface area or volume. In embodiments of the invention, the fractal antenna can be implemented as an inductive circuit. In embodiments of the invention, the fractal antenna 460 can be secured to the inside/outside of the IC housing 450. In some embodiments of the invention, the fractal antenna 460 is provided inside the IC housing 450 in/one one of the substrates of the IC 102B.

The thicknesses of the respective layers of the novel biosensing IC 102B described herein can vary according to design considerations. For example, the thicknesses of the layers of the novel biosensing IC 102B can be designed to have predetermined thicknesses, to have thicknesses within predetermined ranges, to have thicknesses having fixed ratios with respect to each other, or to have thicknesses based on any other consideration or combination of considerations in accordance with the various functionalities described herein.

Figure 5:
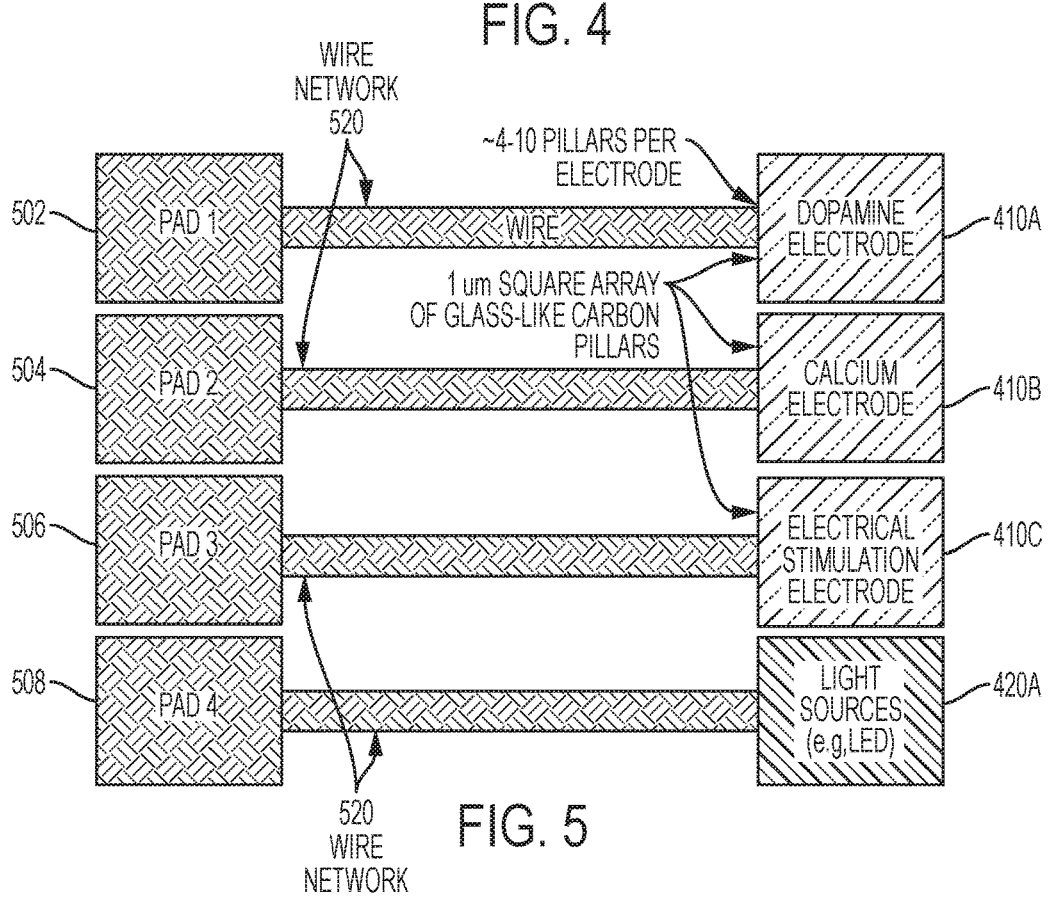
FIG. 5 depicts diagram showing a top-down view of an example sensors and wiring layout of an IC with a nanometer scale biosensor according to embodiments of the invention.

FIG. 5 depicts diagram showing a top-down view of an example layout of the sensors/electrodes 410A, 410B, 410C, light sources 420A, contact pads 502, 504, 506, 508, and wire network 520. Electrical stimulation electrode 410C is the auxiliary electrode for implementing FSCV measurements techniques. FIG. 5 clarifies that multiple types of electrodes/sensors can be provided. FIG. 5 further illustrates that through the contact pads 502, 504, 506, 508 and the wire network 520 each electrode 410A, 410B, 410C and light source 420A can be accessed individually in order to map out a more complete and granular analysis of the neurological behavior of the various chemicals the biosensing IC 102B is configured to detect.

FIGS. 6-23 illustrate an exemplary method for forming a biosensing system 402A according to embodiments of the invention. The biosensing system 402A shown in FIGS. 6-23 is an example implementation of the biosensing system 402 shown in FIG. 4. In the example illustrated in FIGS. 6-23, the biosensing system 402A is implemented using semiconductor fabrication techniques, wherein the interconnect network 230, 430 (shown in FIGS. 2 and 4) represented by pad 1602 (shown in FIG. 16) is formed after forming the glass-like carbon 1002A. General descriptions of semiconductor device fabrication processes that can be utilized in implementing the biosensing system 402A according to embodiments of the present invention will now be provided. Although specific fabrication operations used in implementing the biosensing system 402A can be individually known, the described combination of operations and/or resulting structures of the present invention are unique. Thus, the unique combinations of the operations described according to the present invention utilize a variety of individually known physical and chemical processes performed on a semiconductor (e.g., silicon) substrate, some of which are described in more detail in the immediately following paragraphs.

Figure 6:
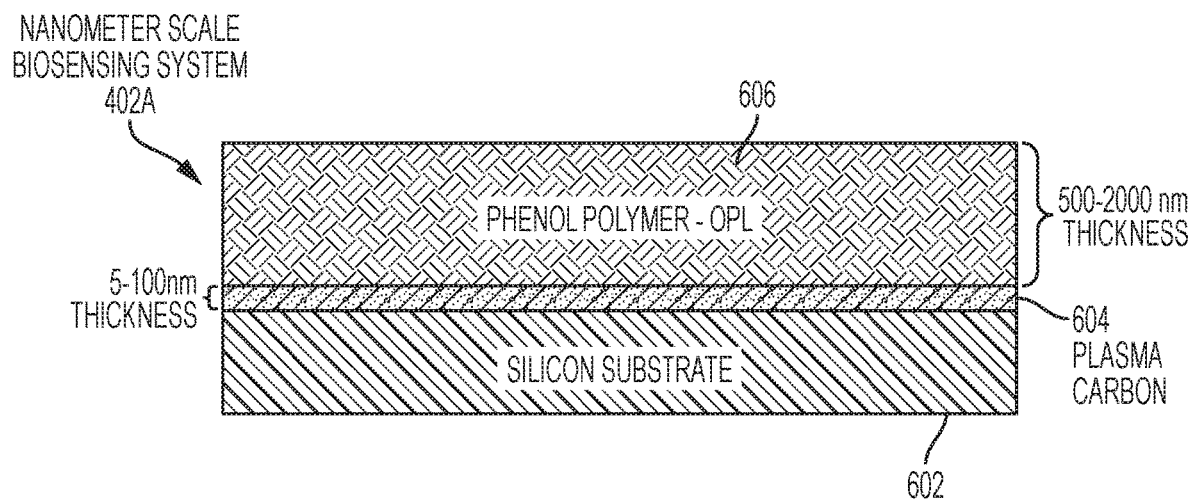
FIG. 6 depicts a cross-sectional view of an IC with a nanometer scale biosensor after an initial fabrication stage according to embodiments of the invention.

FIG. 6 depicts a cross-sectional view of the biosensing system 402A after an initial fabrication stage according to embodiments of the invention. In the fabrication stage shown in FIG. 6, a film stack is formed for adhesion optimization using conventional fabrication techniques. The film stacks include a substrate 602, a layer of plasma carbon 604, and a layer of phenol polymer OPL 606. In embodiments of the invention, the PECVD carbon 604 is a carbon-rich film (e.g., from about 80% to about 100% carbon), which corresponds to the enhanced adhesive/physical coupling region 212 (shown in FIG. 2). In embodiments of the invention, the plasma carbon is deposited using CVD. In embodiments of the invention, the OPL 606 can be deposited using a spin coating technique.

Figure 7:
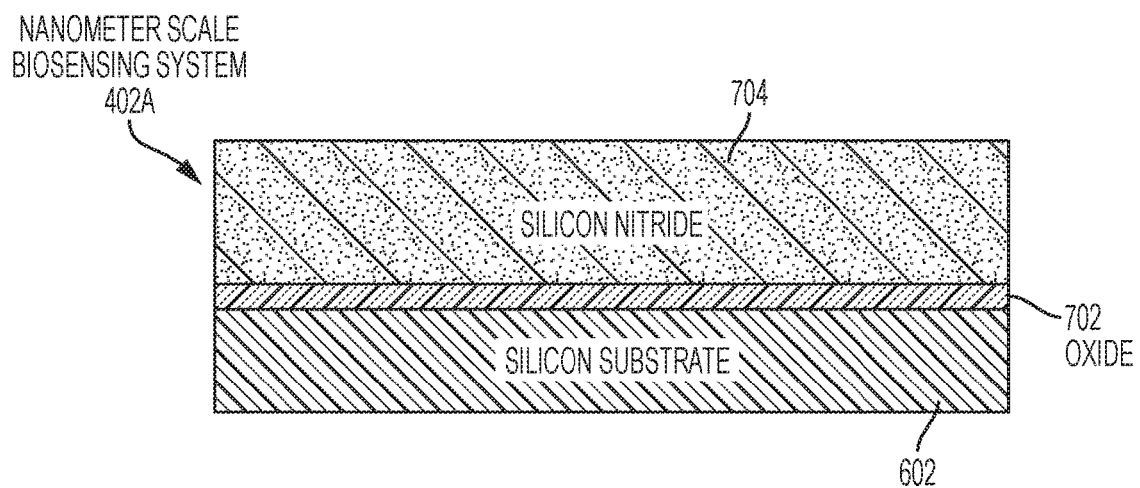
FIG. 7 depicts a cross-sectional view of an IC with a nanometer scale biosensor after an initial fabrication stage according to embodiments of the invention.

FIG. 7 depicts a cross-sectional view of the biosensing system 402A after an alternative initial fabrication stage according to embodiments of the invention. In the fabrication stage shown in FIG. 7, an alternate film stack is formed for adhesion optimization using conventional fabrication techniques. The alternate film stacks include the substrate 602, a layer of oxide 702, and a layer of silicon nitride 704. The layer of oxide 702 and the layer of silicon nitride 704 will be used to form locking regions 902 (shown in FIGS. 9-23). In embodiments of the invention, multiple thin layers of nitride 704 and oxide 702 can be provided in order to create multiple binding crevices for the cured glass-like carbon (e.g., glass-like carbon 1002A shown in FIG. 11).

Figure 8:
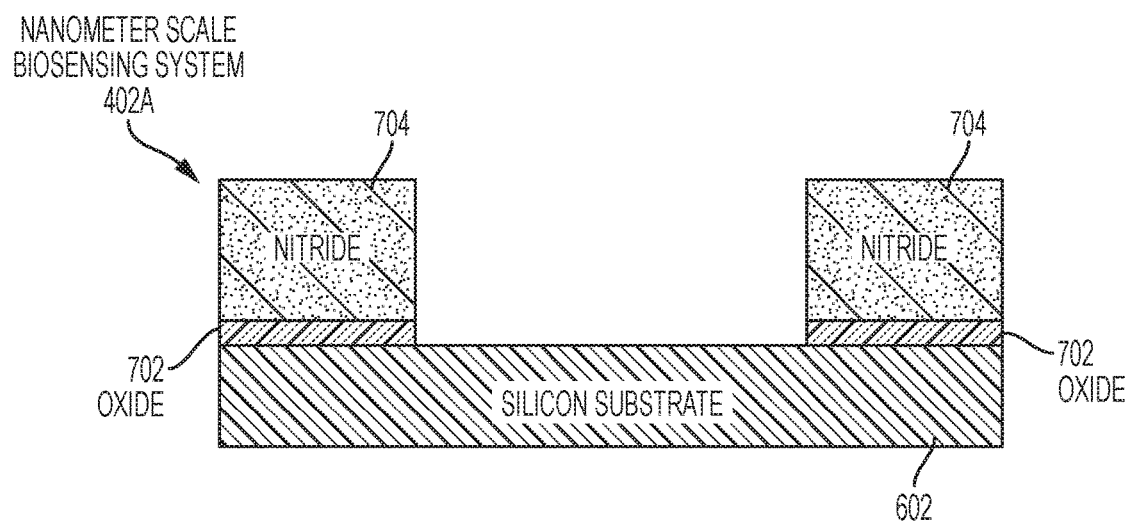
FIG. 8 depicts a cross-sectional view of the IC with a nanometer scale biosensor after a fabrication stage according to embodiments of the invention.

In FIG. 8, the interconnect network 230, 430 (shown in FIGS. 2 and 4) is patterned and the nitride 704/oxide 702 layers are stripped.

Figure 9:
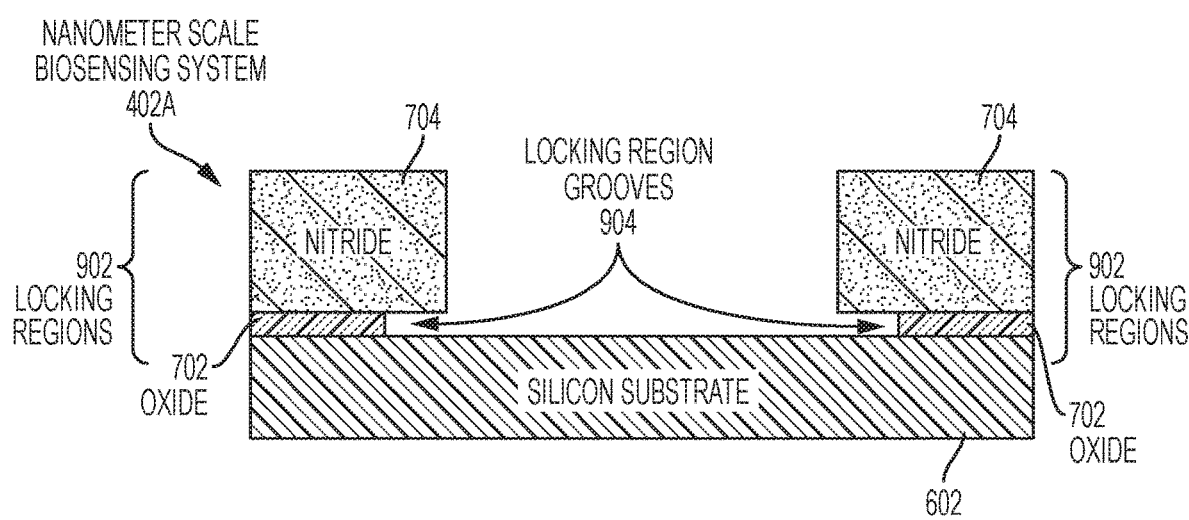
FIG. 9 depicts a cross-sectional view of the IC with a nanometer scale biosensor after a fabrication stage according to embodiments of the invention.

In FIG. 9, a wet etch or isotropic plasma etch is performed to form the locking regions 902 and the laterally extending locking region groves 904. Alternatively, the laterally extending locking region groves 904 could be formed directly in the substrate 602.

Figure 10:
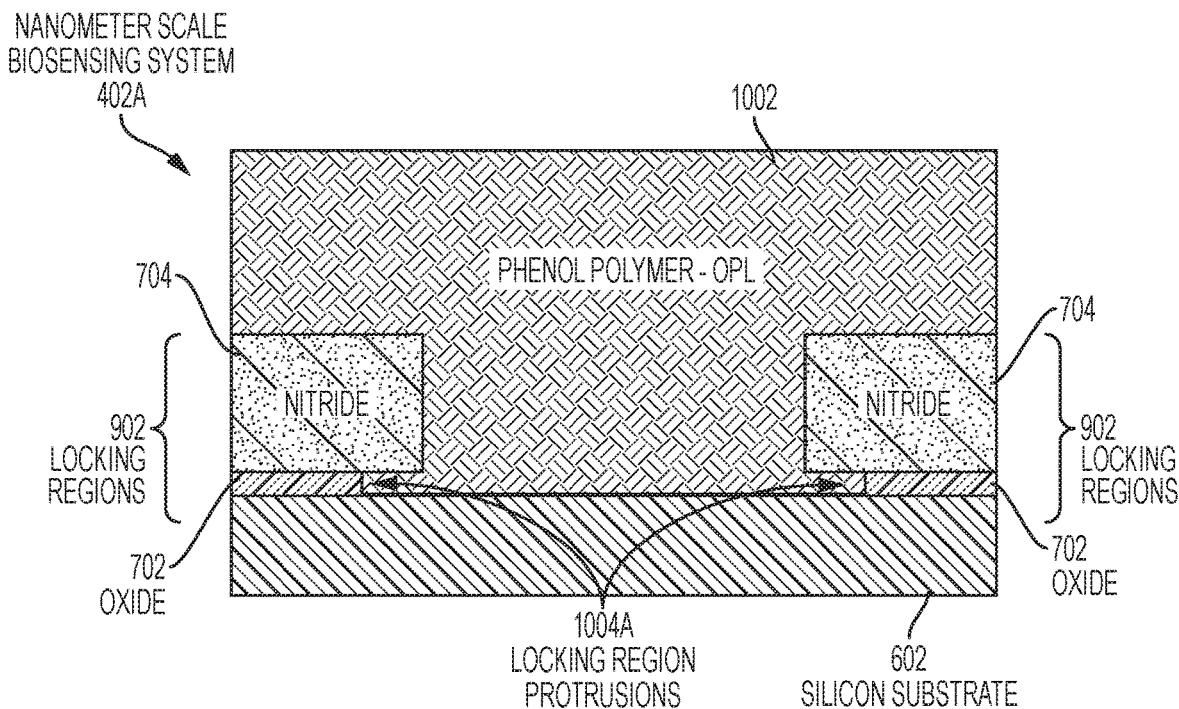
FIG. 10 depicts a cross-sectional view of the IC with a nanometer scale biosensor after a fabrication stage according to embodiments of the invention.

In FIG. 10, a phenol polymer OPL 1002 is deposited using conventional fabrication techniques. In embodiments of the invention, the phenol polymer OPL 1002 can be deposited using a spin coating technique. The phenol polymer OPL 1002 includes locking region protrusions 1004 that extend laterally into the locking region grooves 904 (shown in FIG. 9).

Figure 11:
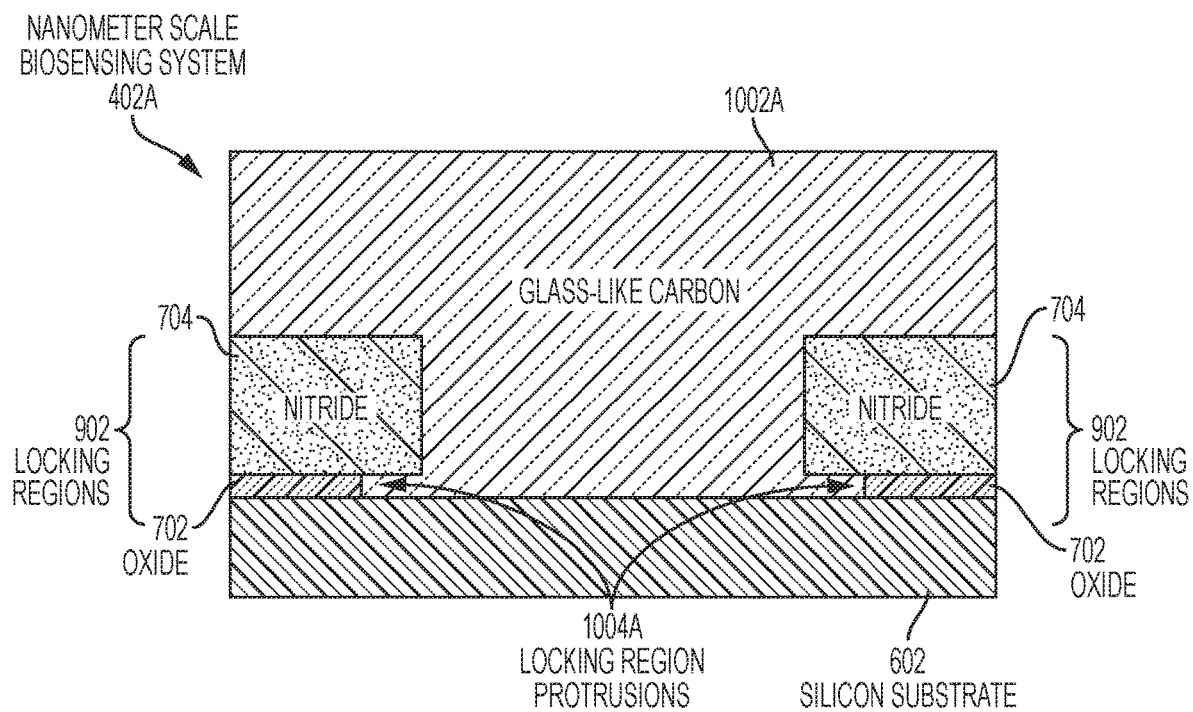
FIG. 11 depicts a cross-sectional view of the IC with a nanometer scale biosensor after a fabrication stage according to embodiments of the invention.

In FIG. 11, a high temperature anneal (e.g., from about 900 Celsius degrees to about 1200 Celsius degrees) is applied to the biosensing system 402A to convert the phenol polymer OPL 1002 to a glass-like carbon 1002A. The glass-like carbon 1002A has locking region protrusions 1004A that extend laterally into the locking region grooves 904 (shown in FIG. 9). The glass-like carbon 1002A shrinks relative to the pre-high-temperature-anneal phenol polymer OPL 1002. The fit between the locking region protrusions 1004A and the locking region grooves 904 (shown in FIG. 9) serves to ensure that shrinkage from the high temperature anneal does not delaminate the glass-like carbon 1002A from the substrate 602. The high temperature anneal will densify the nitride 704 and/or the oxide 702, which can enhance their stability and counter post-anneal shrinkage in the glass-like carbon materials. Also, in embodiments where the enhanced adhesive/physical coupling region 210 (shown in FIG. 2) includes both locking regions 902 and a plasma carbon 3402 (shown in FIG. 34), the high temperature anneal will cause direct carbon to carbon bonding across the interface of the OPL/glass-like carbon layer 1002A and the PECVD deposited carbon plasma layer 3402.

Figure 12:
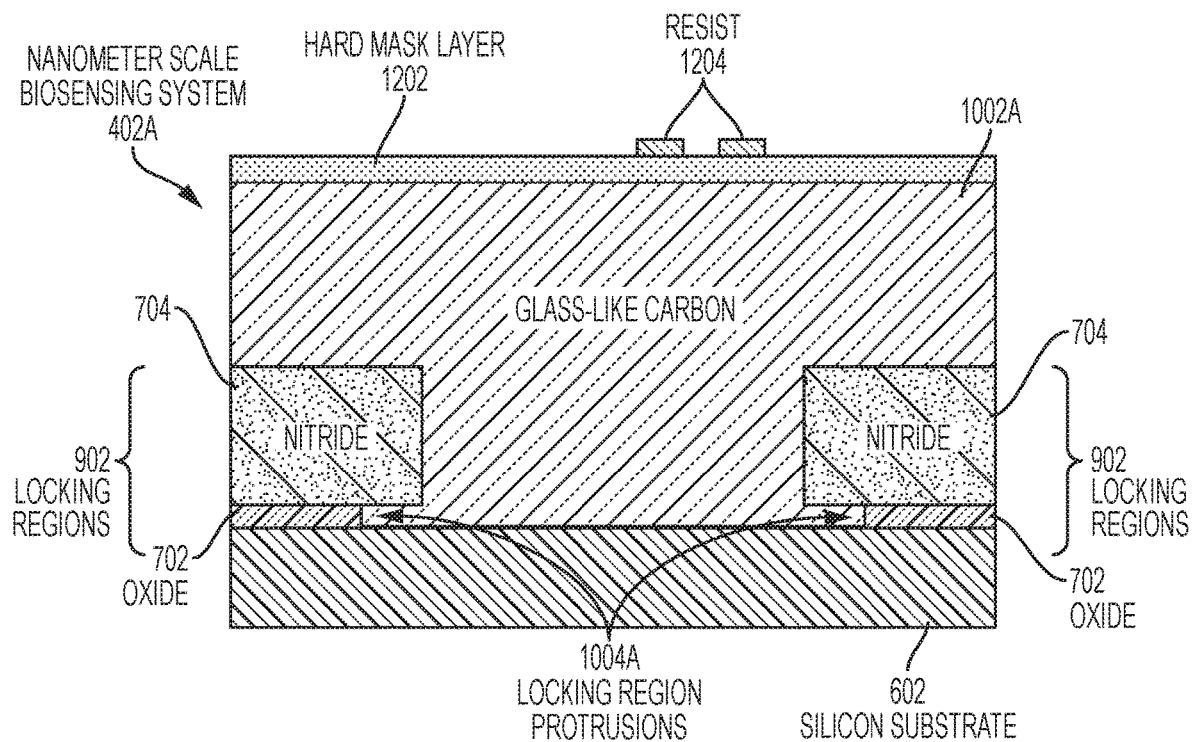
FIG. 12 depicts a cross-sectional view of the IC with a nanometer scale biosensor after a fabrication stage according to embodiments of the invention.
Figure 13:
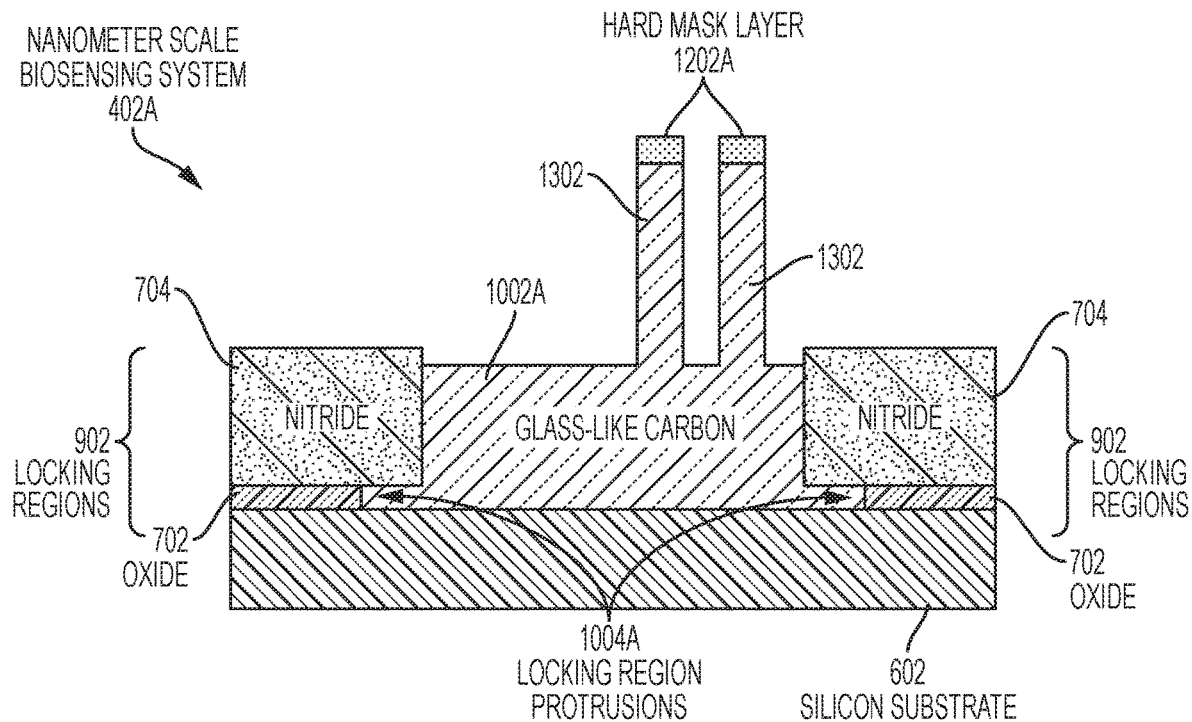
FIG. 13 depicts a cross-sectional view of the IC with a nanometer scale biosensor after a fabrication stage according to embodiments of the invention.

In FIG. 12, a hard mask layer 1202 has been deposited, along with a photo resist pattern 1204 for defining the pillars 1302 (shown in FIG. 13). In embodiments of the invention, the hard mask layer 1202 can be formed from titanium.

In FIG. 13, the glass-like carbon 1002A and the hard mask layer 1202 have been etched to formed the hard masks 1202A and the glass-like carbon pillars 1302 in the glass-like carbon 1002A.

Figure 14:
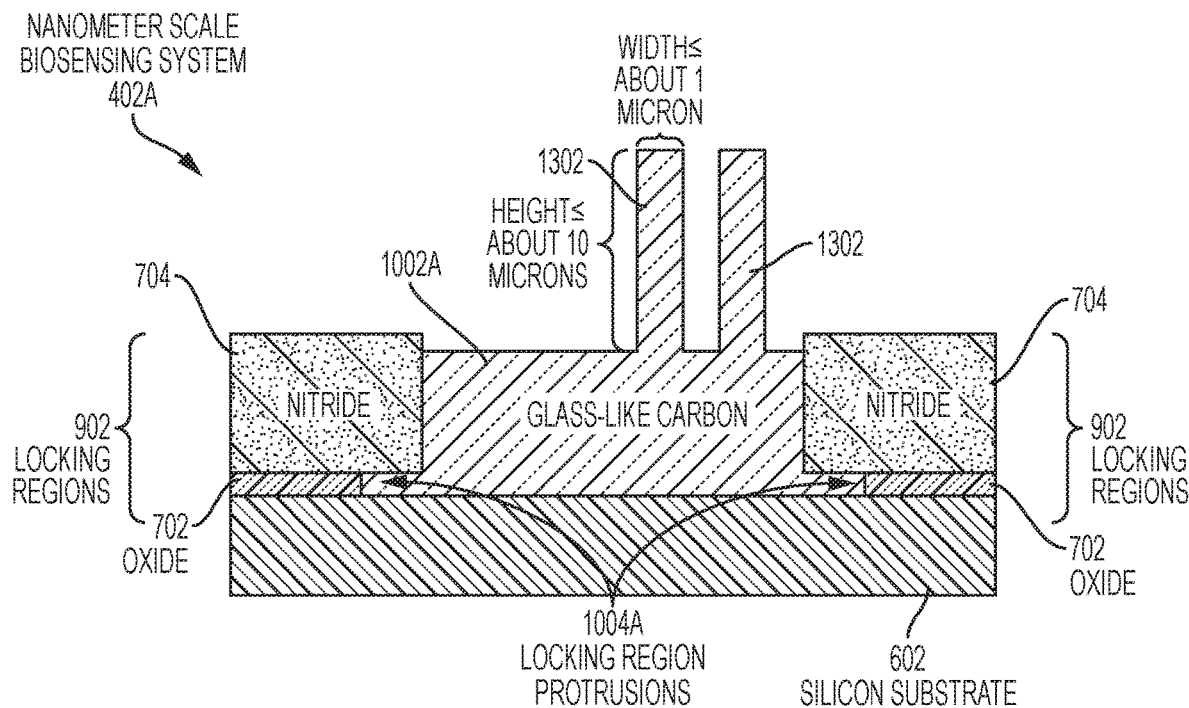
FIG. 14 depicts a cross-sectional view of the IC with a nanometer scale biosensor after a fabrication stage according to embodiments of the invention.

In FIG. 14, the hard masks 1202A have been removed using conventional fabrication techniques (e.g., applying hydrogen peroxide or dilute hydrofluoric acid (DHF)). As depicted in FIG. 14, each of the pillars 1302 has a height dimension that is less than about 10 microns and a width dimension that is less than about 1 micron.

Figure 15:
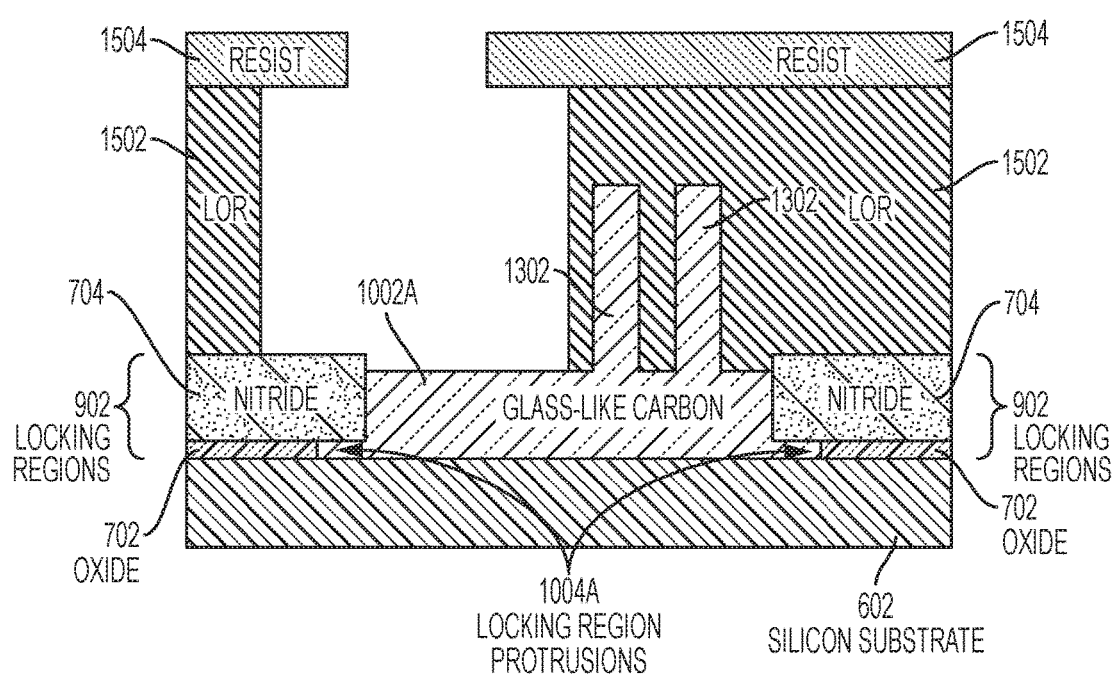
FIG. 15 depicts a cross-sectional view of the IC with a nanometer scale biosensor after a fabrication stage according to embodiments of the invention.

In FIG. 15, lift off resist (LOR) 1502 and lithography resist 1504 are deposited for defining the interconnect network 230, 430 (shown in FIGS. 2 and 4), which includes the pads 502, 504, 506, 508 (shown in FIG. 5) the wire network 520 (shown in FIG. 5) and through-silicon-vias (not shown).

Figure 16:
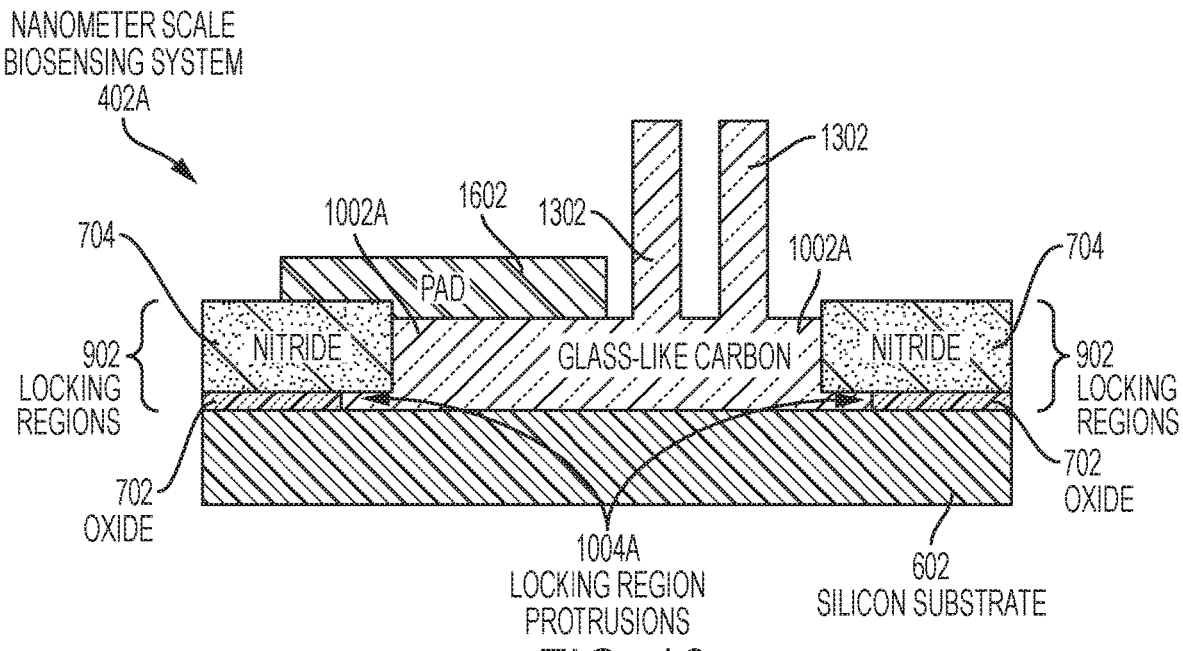
FIG. 16 depicts a cross-sectional view of an IC with a nanometer scale biosensor after an initial fabrication stage according to embodiments of the invention.

In FIG. 16, metal has been deposited to form the interconnect network 230, 430 (shown in FIGS. 2 and 4), which includes the pads 502, 504, 506, 508 (shown in FIG. 5) the wire network 520 (shown in FIG. 5) and through-silicon-vias (not shown). Only a pad 1602 of the interconnect network 230, 430 is depicted in FIG. 16. The not shown). The LOR 1502 and lithography resist 1504 have been dissolved and removed.

Figure 17:
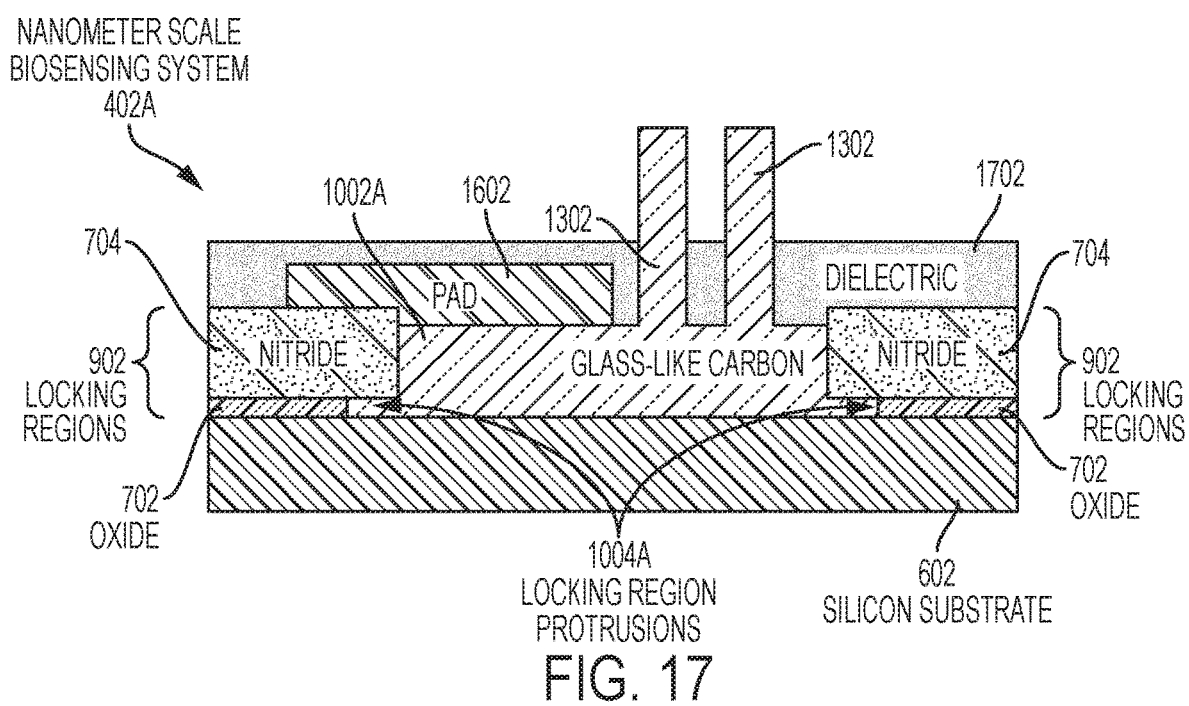
FIG. 17 depicts a cross-sectional view of the IC with a nanometer scale biosensor after a fabrication stage according to embodiments of the invention.

In FIG. 17, a dielectric layer 1702 is deposited using conventional fabrication techniques. In embodiments of the invention, the dielectric 11702 can be deposited using a spin coating technique.

Figure 18:
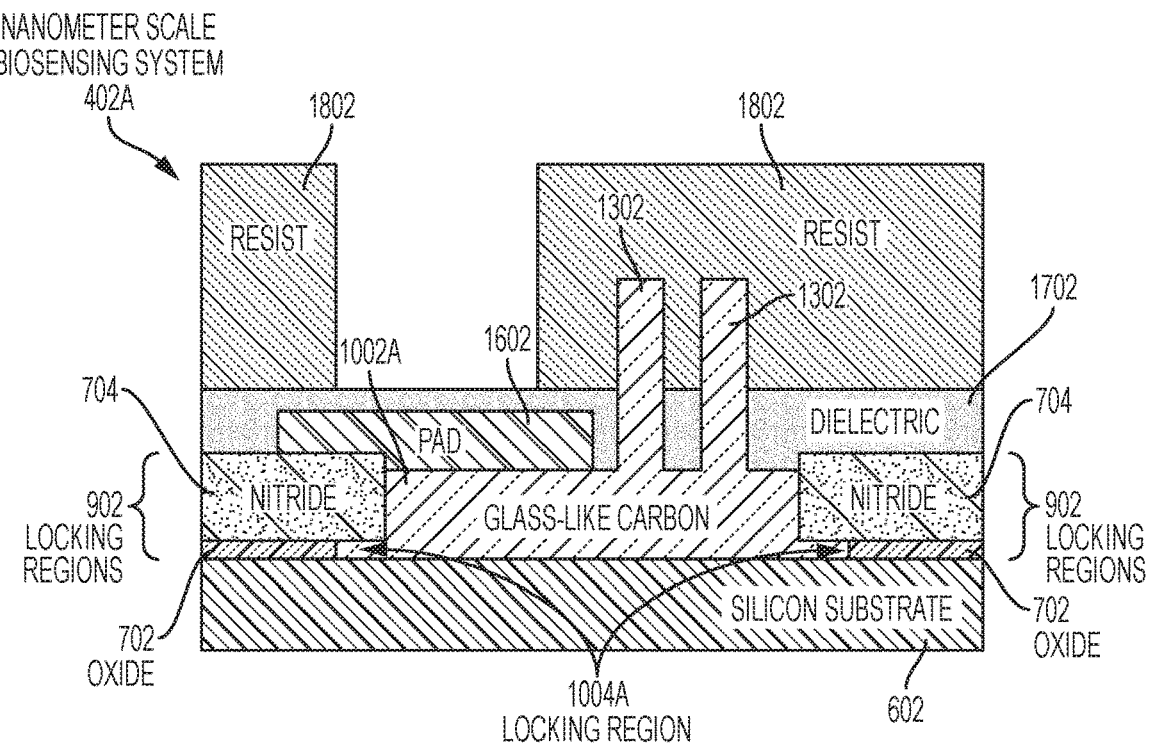
FIG. 18 depicts a cross-sectional view of the IC with a nanometer scale biosensor after a fabrication stage according to embodiments of the invention.

In FIG. 18, a photo resist pattern 1802 is deposited. The resist pattern 102 defines an area of the dielectric 1702 that will be removed in order to access a surface of the pad 1602 (e.g., using a probe).

Figure 19:
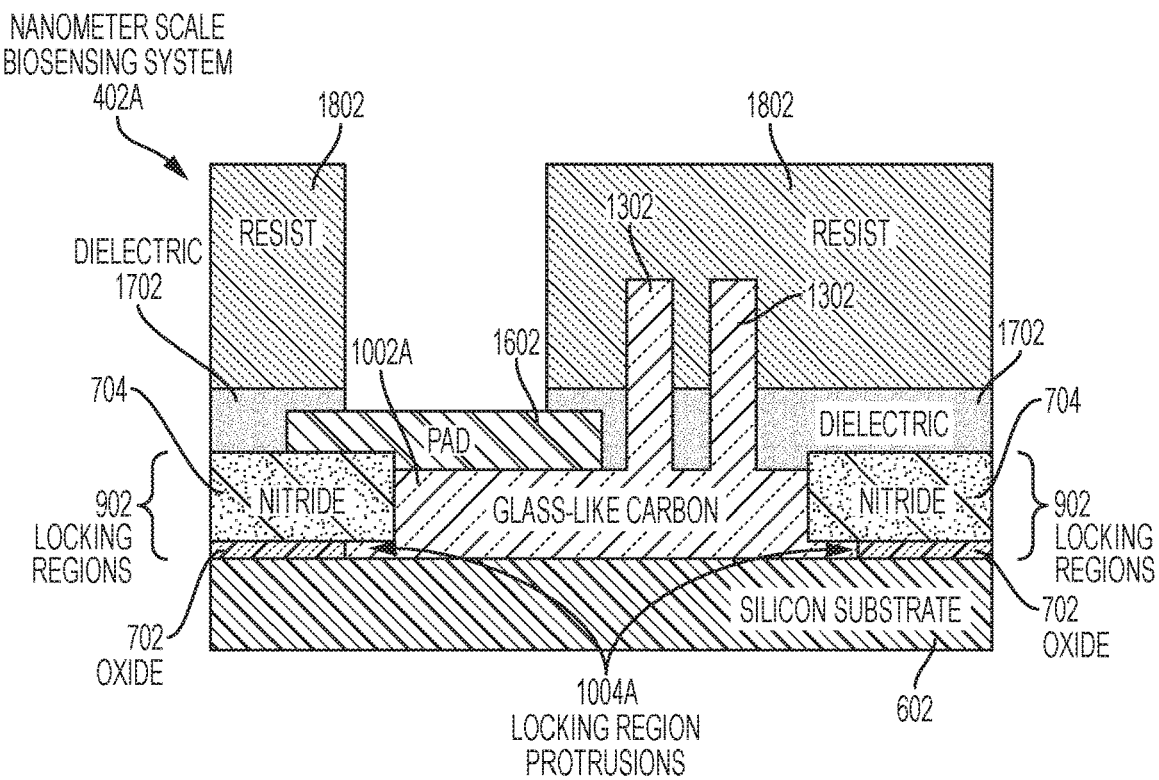
FIG. 19 depicts a cross-sectional view of the IC with a nanometer scale biosensor after a fabrication stage according to embodiments of the invention.

In FIG. 19, the area of the dielectric 1702 has been removed using a wet or dry etch (e.g., RIE) processes.

Figure 20:
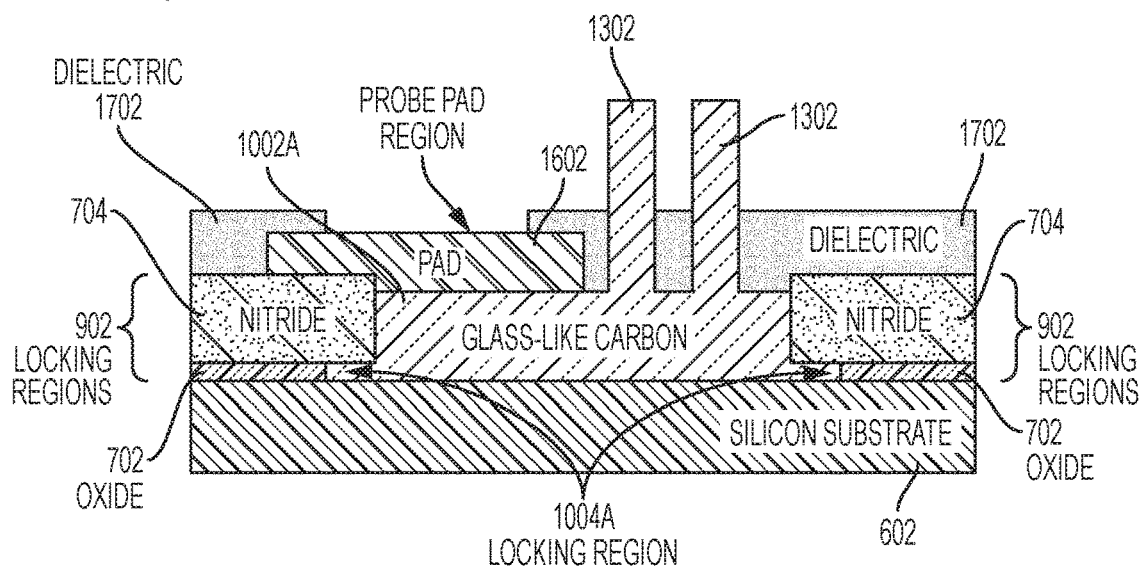
FIG. 20 depicts a cross-sectional view of the IC with a nanometer scale biosensor after a fabrication stage according to embodiments of the invention.

In FIG. 20, the photo resist pattern 1802 has been removed using conventional fabrication techniques.

Figure 21:
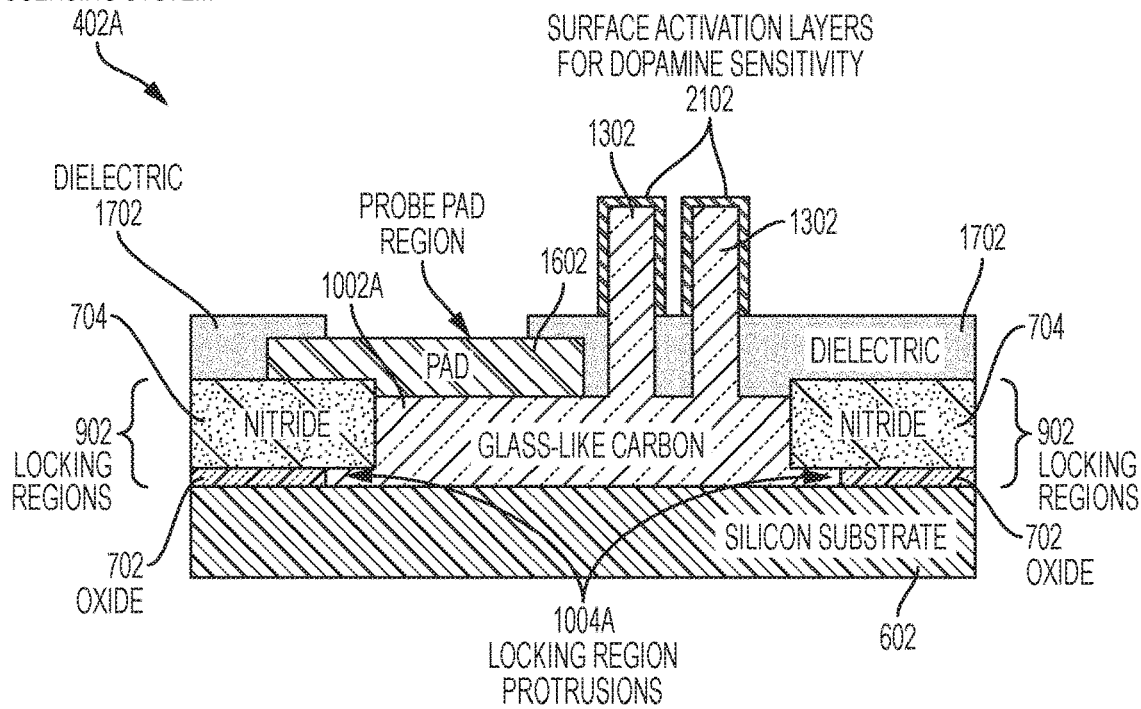
FIG. 21 depicts a cross-sectional view of the IC with a nanometer scale biosensor after a fabrication stage according to embodiments of the invention.
Figure 22:
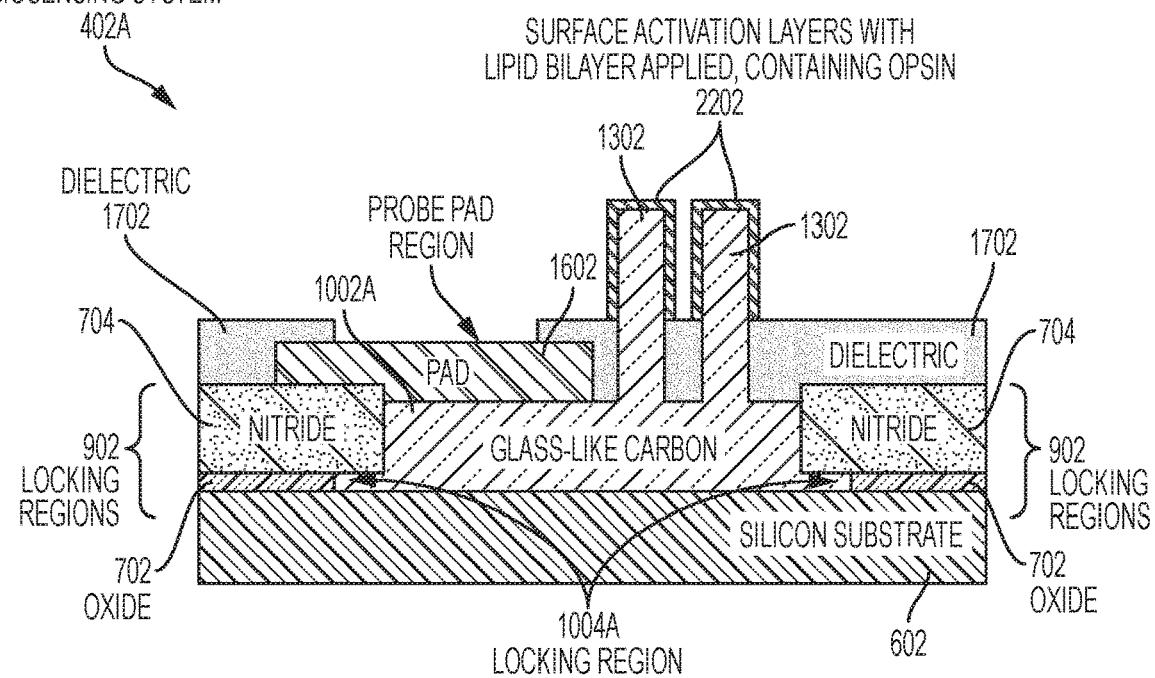
FIG. 22 depicts a cross-sectional view of an IC with a nanometer scale biosensor after a fabrication stage according to embodiments of the invention.
Figure 23:
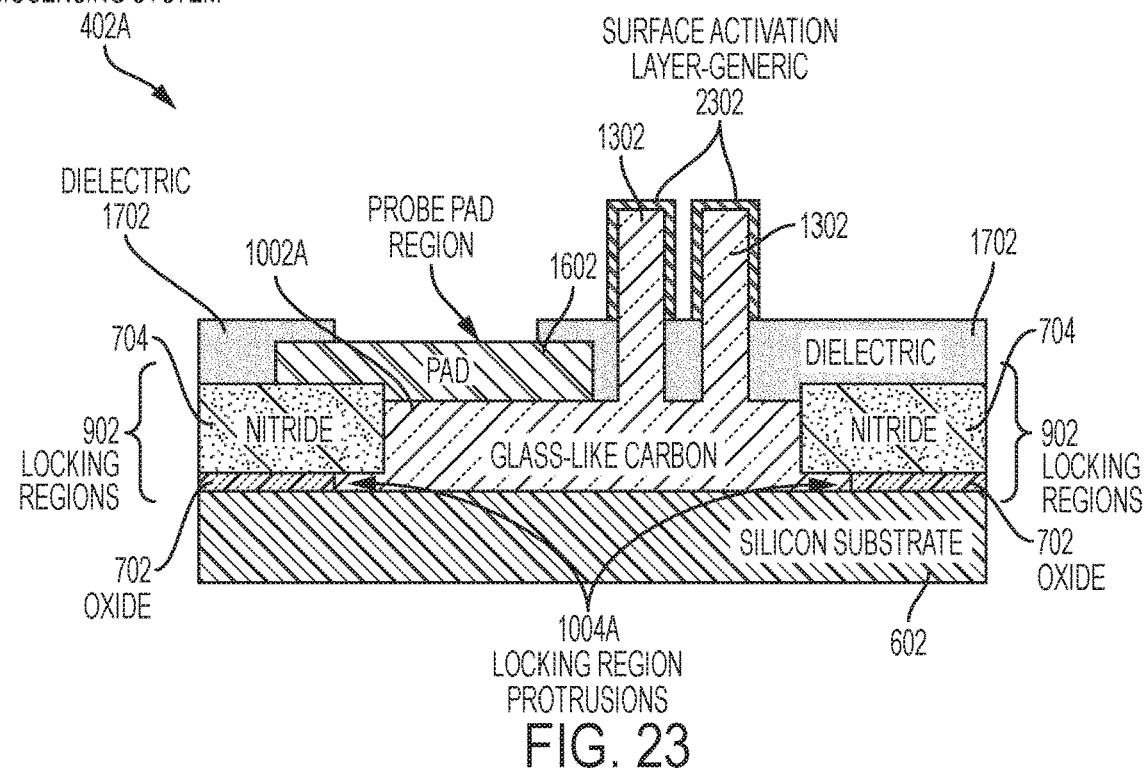
FIG. 23 depicts a cross-sectional view of an IC with a nanometer scale biosensor after a fabrication stage according to embodiments of the invention.

In FIGS. 21, 22 and 23, the exposed surfaces of the pillars 1302 are functionalized to enhance and make more specific the molecules that the pillars 1302 will detect. In FIG. 21, dopamine activation layers 1202 has been applied to the pillars 1302 to make the pillars 1302 more sensitive to detect dopamine. In FIG. 22, a lipid bilayer activation layers 2202 has been applied to the pillars 1302 to make the pillars 1302 more sensitive to detect calcium. In FIG. 22, generic activation layers 2302 has been applied to the pillars 1302 to make the pillars 1302 more sensitive to detect a generic molecule.

FIGS. 24-40 illustrate an exemplary method for forming a nanometer scale biosensing system 402B according to embodiments of the invention. The biosensing system 402B shown in FIGS. 24-40 is an example implementation of the biosensing system 402 shown in FIG. 4. In the example illustrated in FIGS. 24-40, the biosensing system 402B is implemented using semiconductor fabrication techniques, wherein the interconnect network 2802 (shown in FIG. 28) is formed before forming the glass-like carbon 3502A. General descriptions of semiconductor device fabrication processes that can be utilized in implementing the biosensing system 402B according to embodiments of the present invention will now be provided. Although specific fabrication operations used in implementing the biosensing system 402B can be individually known, the described combination of operations and/or resulting structures of the present invention are unique. Thus, the unique combinations of the operations described according to the present invention utilize a variety of individually known physical and chemical processes performed on a semiconductor (e.g., silicon) substrate, some of which are described in more detail in the immediately following paragraphs.

Figure 24:
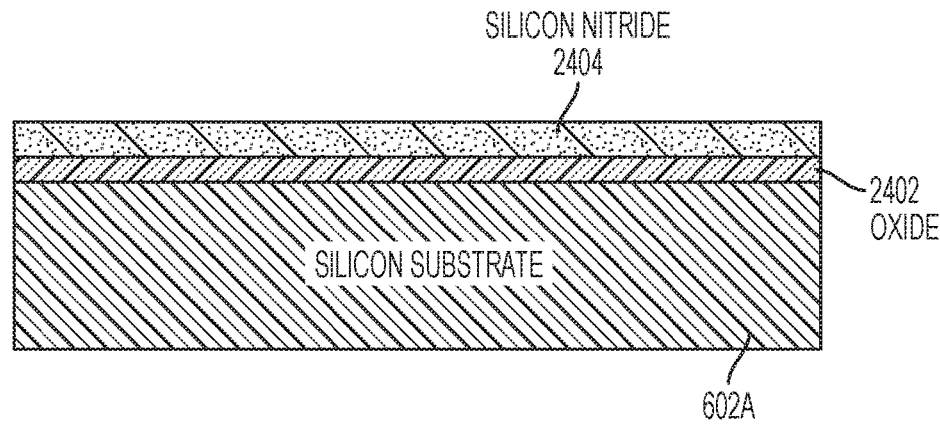
FIG. 24 depicts a cross-sectional view of an IC with a nanometer scale biosensor after a fabrication stage according to embodiments of the invention, wherein the biosensor system wiring is formed under the biosensor electrode according to embodiments of the invention.

FIG. 24 depicts a cross-sectional view of the biosensing system 402B after an initial fabrication stage according to embodiments of the invention. In the fabrication stage shown in FIG. 24, a film stack is formed using conventional fabrication techniques. The film stacks include the substrate 602A, a layer of oxide 2402, and a layer of silicon nitride 2404, which will be subsequently processed to define the interconnect network 2802 (shown in FIG. 28).

Figure 25:
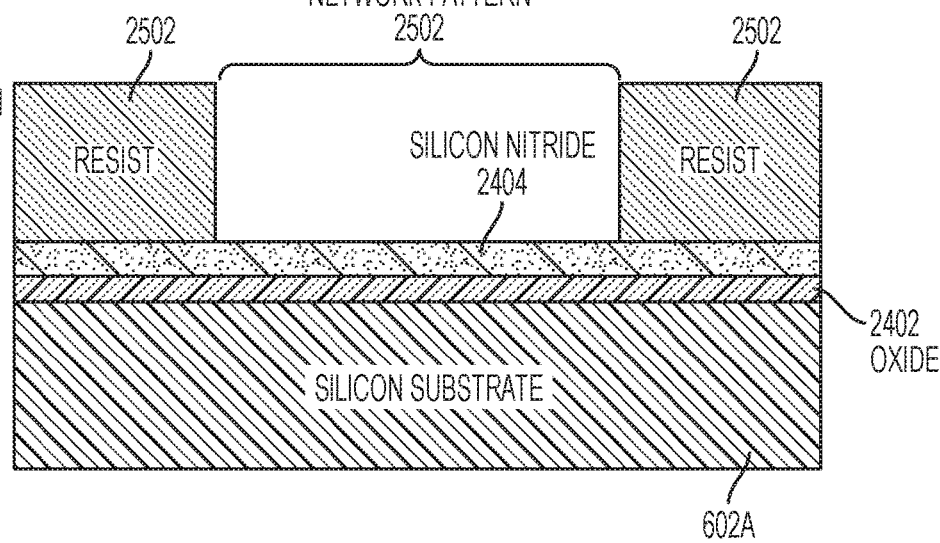
FIG. 25 depicts a cross-sectional view of the IC with a nanometer scale biosensor after a fabrication stage according to embodiments of the invention, wherein the biosensor system wiring is formed under the biosensor electrode according to embodiments of the invention.

In FIG. 25, an interconnect network pattern 2502 is defined using resist 2502.

Figure 26:
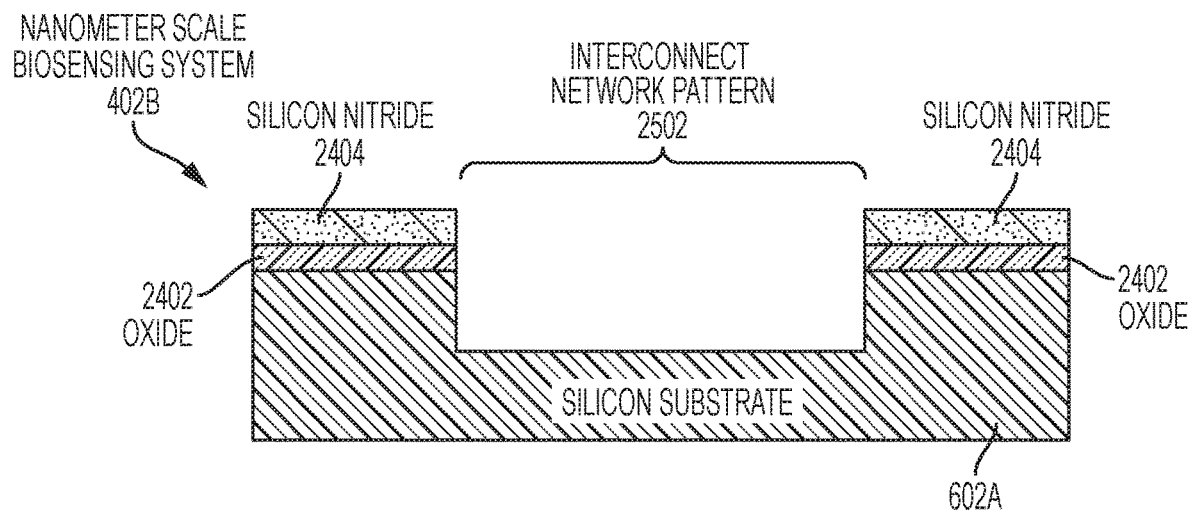
FIG. 26 depicts a cross-sectional view of the IC with a nanometer scale biosensor after a fabrication stage according to embodiments of the invention, wherein the biosensor system wiring is formed under the biosensor electrode according to embodiments of the invention.

In FIG. 26, the interconnect pattern 2502 has been etched into the substrate 602A, and the resist 2502 has been removed.

Figure 27:
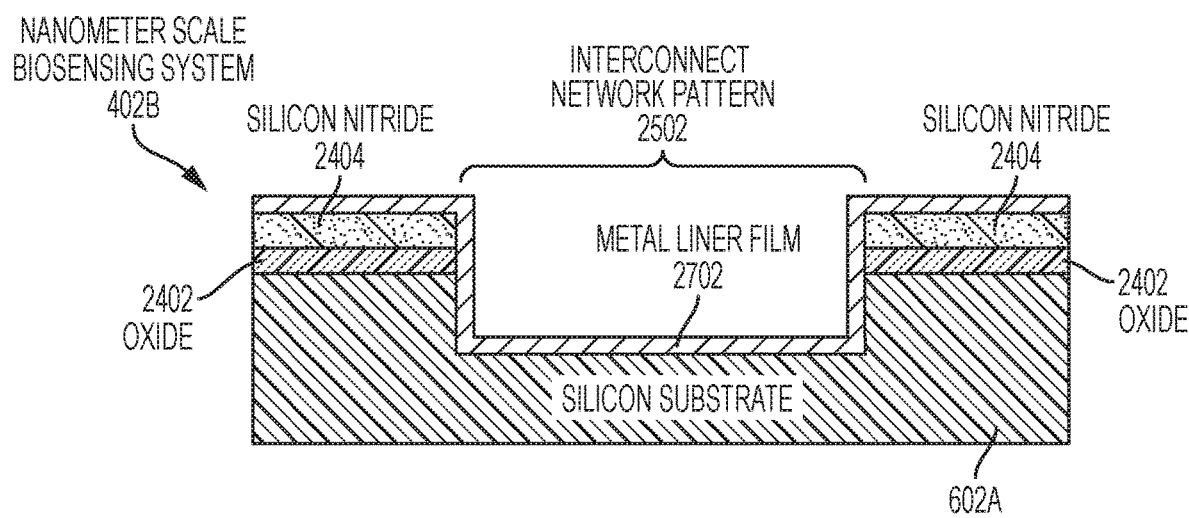
FIG. 27 depicts a cross-sectional view of the IC with a nanometer scale biosensor after a fabrication stage according to embodiments of the invention, wherein the biosensor system wiring is formed under the biosensor electrode according to embodiments of the invention.

In FIG. 27, a metal liner film 2702 is deposited conformally over the biosensing system 402B. In embodiments of the invention, the metal liner film 2702 can be formed from TaN, $TiB_2$, or TiN.

Figure 28:
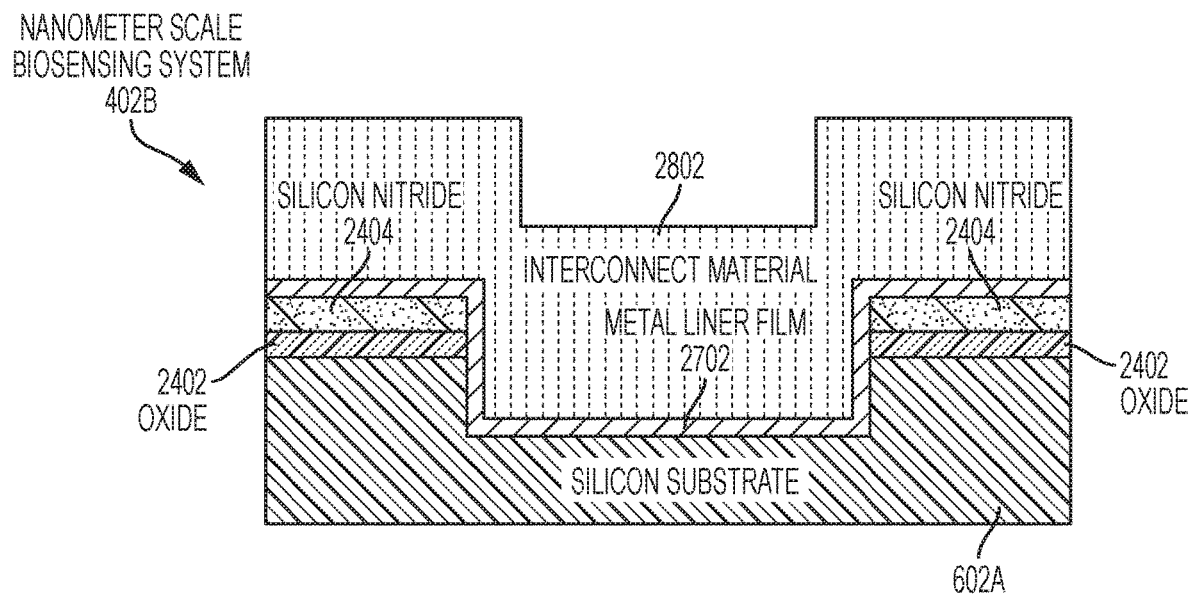
FIG. 28 depicts a cross-sectional view of the IC with a nanometer scale biosensor after a fabrication stage according to embodiments of the invention, wherein the biosensor system wiring is formed under the biosensor electrode according to embodiments of the invention.

In FIG. 28, interconnect material 2802 is deposited using conventional fabrication techniques.

Figure 29:
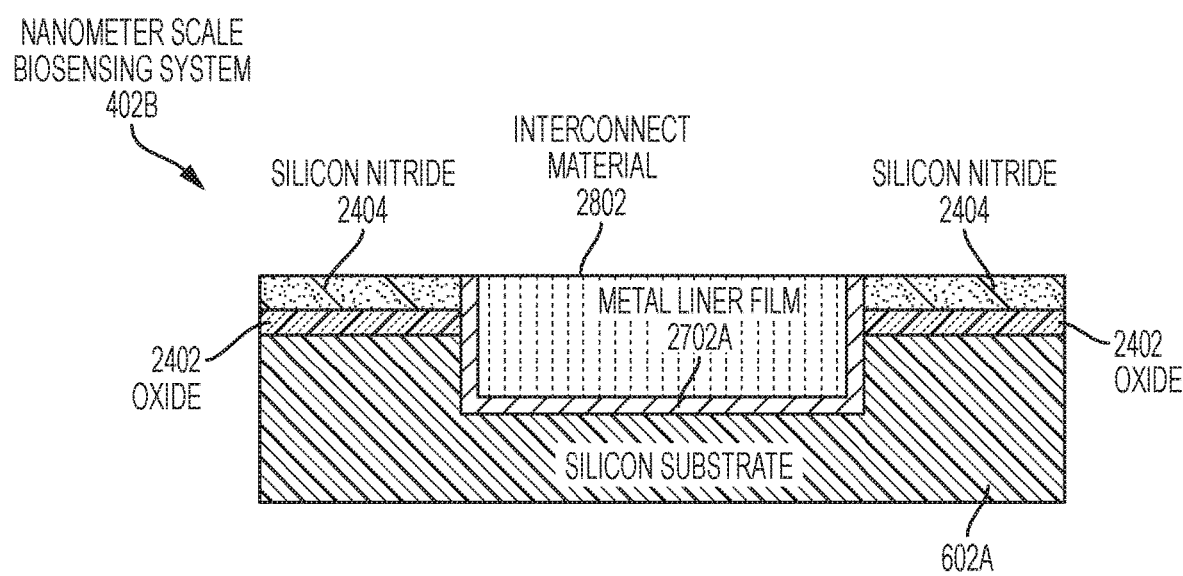
FIG. 29 depicts a cross-sectional view of the IC with a nanometer scale biosensor after a fabrication stage according to embodiments of the invention, wherein the biosensor system wiring is formed under the biosensor electrode according to embodiments of the invention.

In FIG. 29, the interconnect material 2802 and the metal liner film 2702 have been polished back using chemical mechanical polishing (CMP) to form interconnect network 2802A and metal liner film 2702A.

Figure 30:
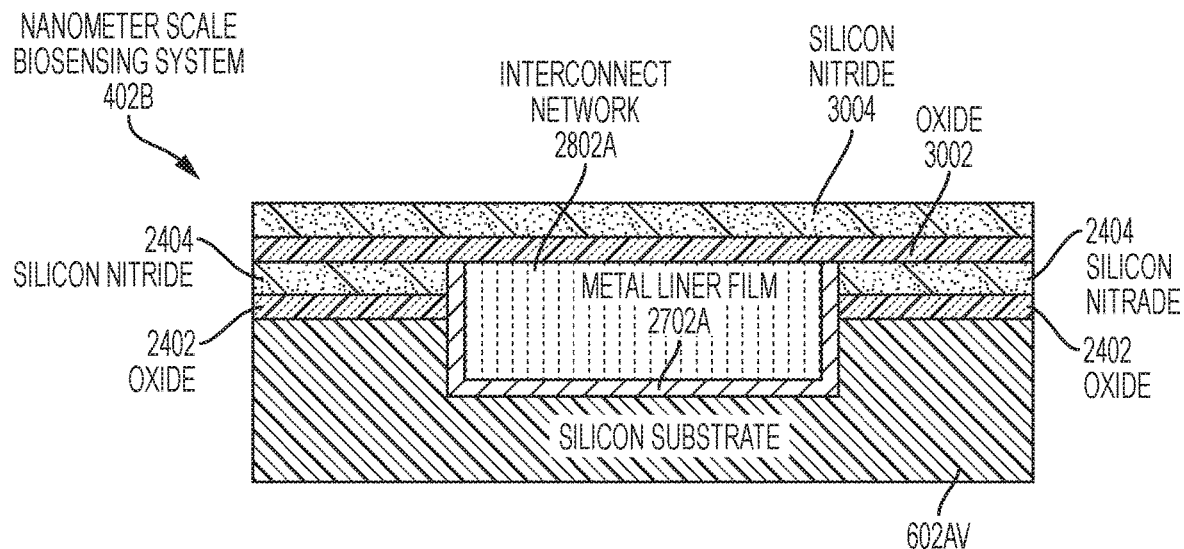
FIG. 30 depicts a cross-sectional view of the IC with a nanometer scale biosensor after a fabrication stage according to embodiments of the invention, wherein the biosensor system wiring is formed under the biosensor electrode according to embodiments of the invention.

In FIG. 30, film stacks are formed for adhesion optimization using conventional fabrication techniques. The film stacks include a layer of oxide 3002 and a layer of silicon nitride 3004. The layer of oxide 3002 and the layer of silicon nitride 3004 will be used to form locking regions 3302 (shown in FIGS. 33-40). In embodiments of the invention, multiple thin layers of the nitride 3004 and the oxide 3002 can be provided in order to create multiple binding crevices for the cured glass-like carbon (e.g., glass-like carbon 3502A shown in FIG. 36).

Figure 31:
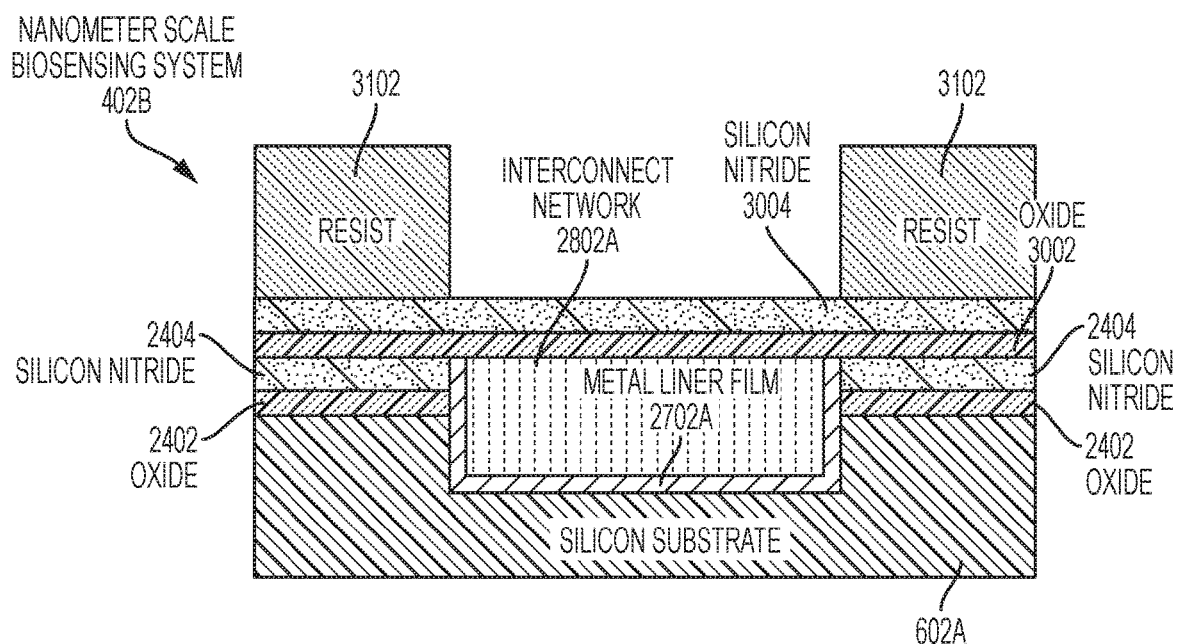
FIG. 31 depicts a cross-sectional view of the IC with a nanometer scale biosensor after a fabrication stage according to embodiments of the invention, wherein the biosensor system wiring is formed under the biosensor electrode according to embodiments of the invention.

In FIG. 31, resist 3102 is deposited to define an opening for accessing the interconnect network 2802A.

Figure 32:
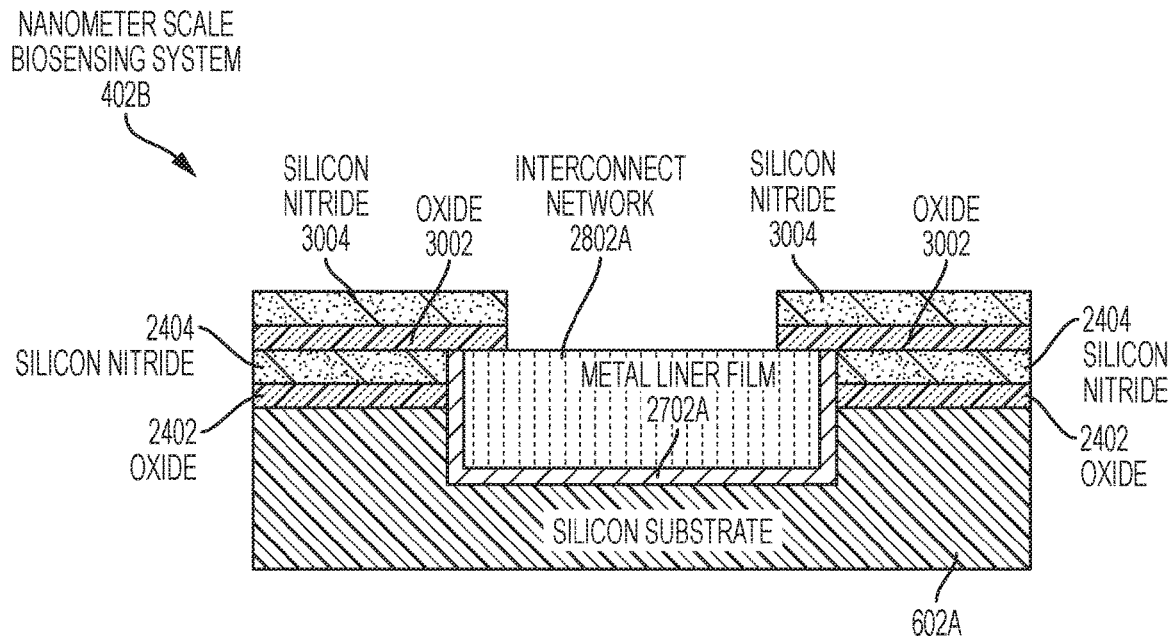
FIG. 32 depicts a cross-sectional view of the IC with a nanometer scale biosensor after a fabrication stage according to embodiments of the invention, wherein the biosensor system wiring is formed under the biosensor electrode according to embodiments of the invention.

In FIG. 32, layer of silicon nitride 3004 and the layer of oxide 3002 have been etched in the open region of the resist 3102, and the resist 3102 has been removed.

Figure 33:
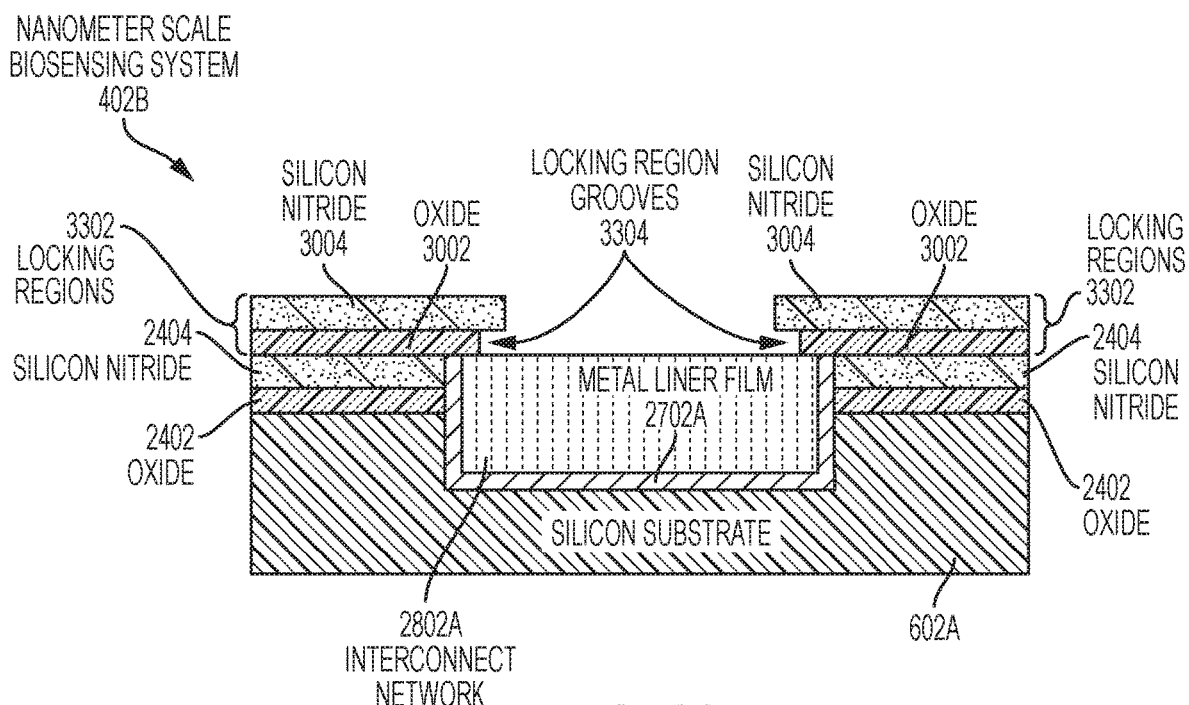
FIG. 33 depicts a cross-sectional view of the IC with a nanometer scale biosensor after a fabrication stage according to embodiments of the invention, wherein the biosensor system wiring is formed under the biosensor electrode according to embodiments of the invention.

In FIG. 33, a wet etch or isotropic etch is performed to form the locking regions 3302 and the laterally extending locking region groves 3304.

Figure 34:
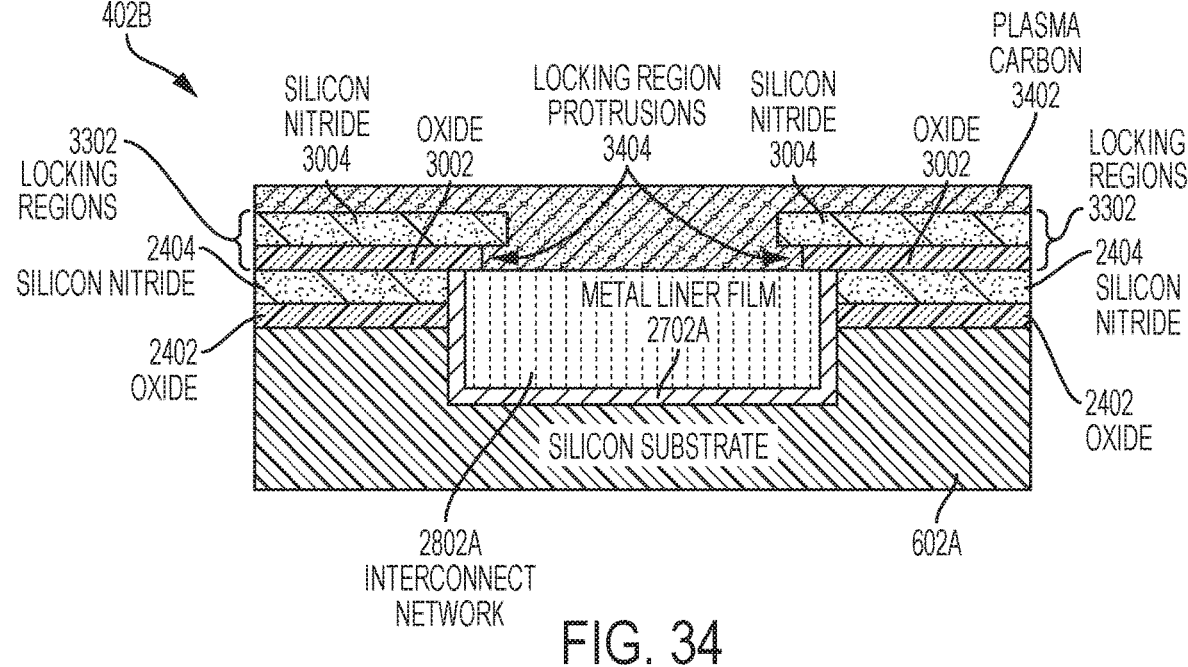
FIG. 34 depicts a cross-sectional view of the IC with a nanometer scale biosensor after a fabrication stage according to embodiments of the invention, wherein the biosensor system wiring is formed under the biosensor electrode according to embodiments of the invention.

In FIG. 34, a layer of carbon-rich plasma 3402 is deposited using conventional fabrication techniques. In embodiments of the invention, the carbon-rich plasma 3402 is deposited using CVD. The carbon-rich plasma 3402 includes locking region protrusions 3404 that extend laterally into the locking region grooves 3304 (shown in FIG. 33).

Figure 35:
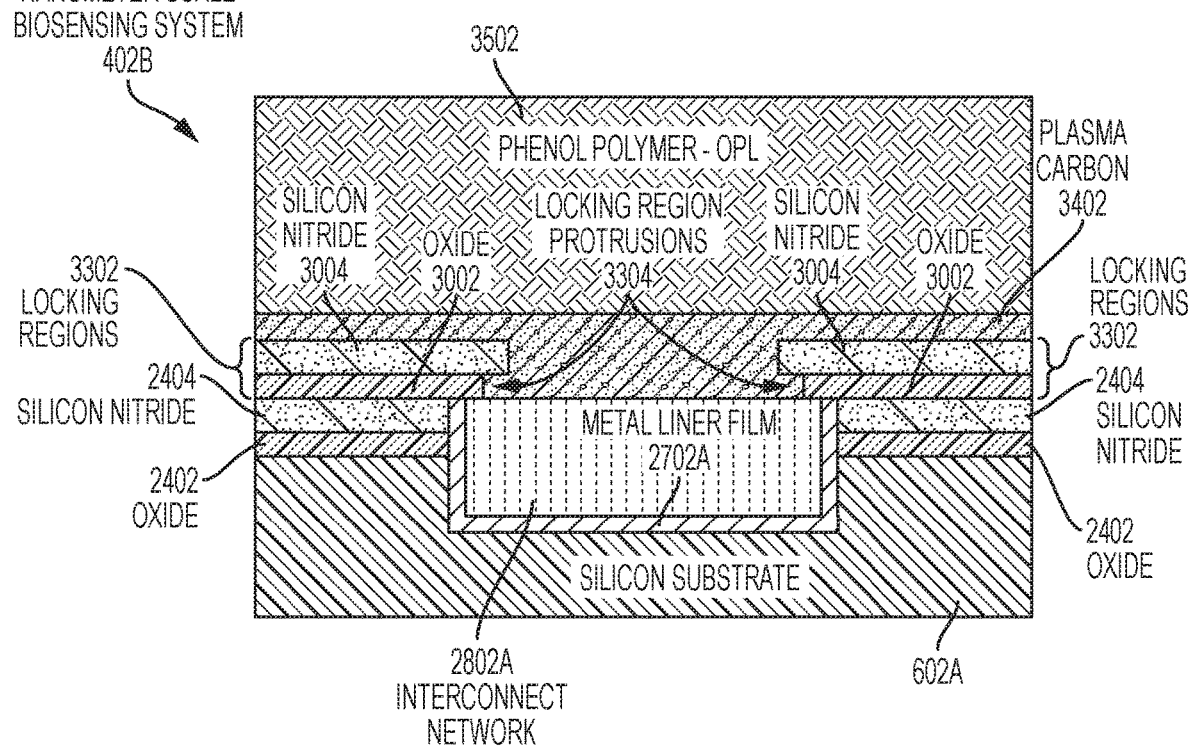
FIG. 35 depicts a cross-sectional view of the IC with a nanometer scale biosensor after a fabrication stage according to embodiments of the invention, wherein the biosensor system wiring is formed under the biosensor electrode according to embodiments of the invention.

In FIG. 35, a phenol polymer OPL 3502 is deposited using conventional fabrication techniques. In embodiments of the invention, the phenol polymer OPL 3502 can be deposited using a spin coating technique.

Figure 36:
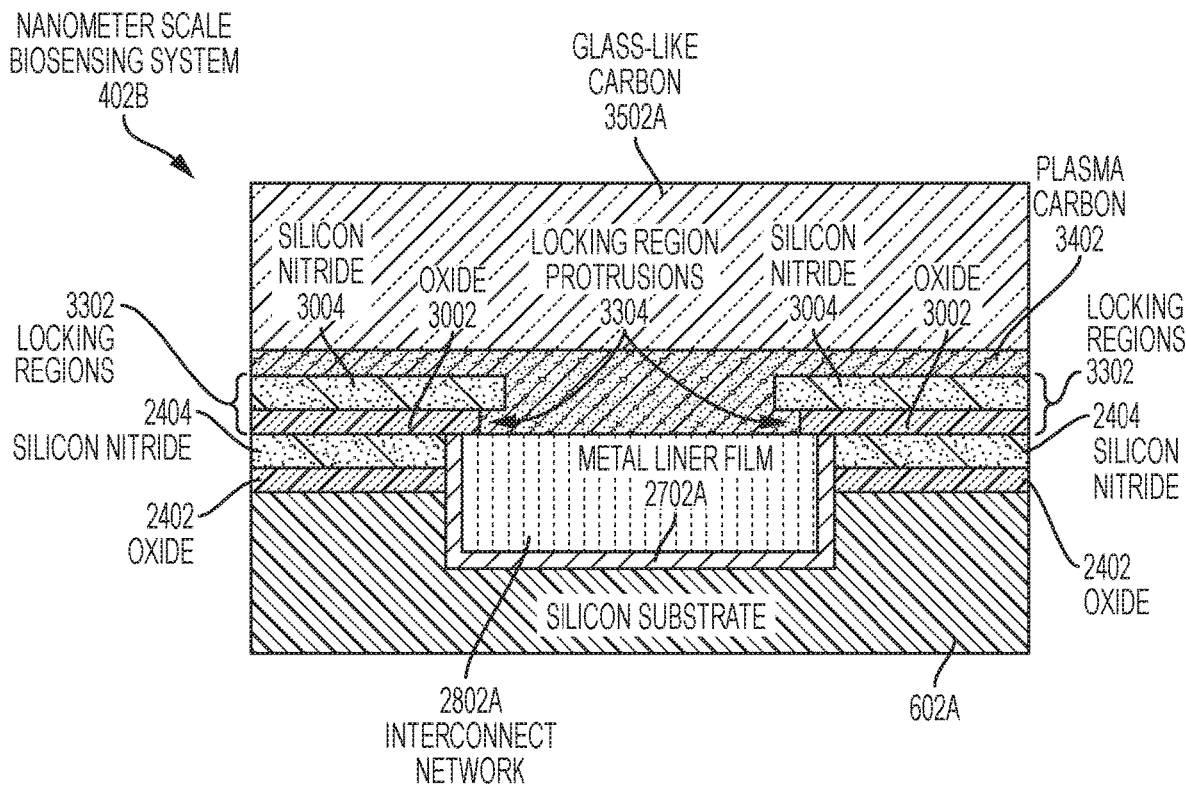
FIG. 36 depicts a cross-sectional view of the IC with a nanometer scale biosensor after a fabrication stage according to embodiments of the invention, wherein the biosensor system wiring is formed under the biosensor electrode according to embodiments of the invention.

In FIG. 36, a high temperature anneal (e.g., from about 900 Celsius degrees to about 1200 Celsius degrees) is applied to the biosensing system 402B to convert the phenol polymer OPL 3502 to a glass-like carbon 3502A. Post high-temperature-anneal, the glass-like carbon 3502A is chemically bound to the carbon in the carbon-rich plasma 3402. The carbon-rich plasma 3402 has locking region protrusions 3404A that extend laterally into the locking region grooves 3304 (shown in FIG. 33). Post-high-temperature-anneal, the carbon-rich plasma 3402 shrinks less than the glass-like carbon 3502A. The fit between the locking region protrusions 3404A and the locking region grooves 3304 (shown in FIG. 33) serves to ensure that shrinkage from the high temperature anneal does not delaminate the carbon-rich plasma 3402 from the interconnect network 2802A and/or the substrate 602A.

Figure 37:
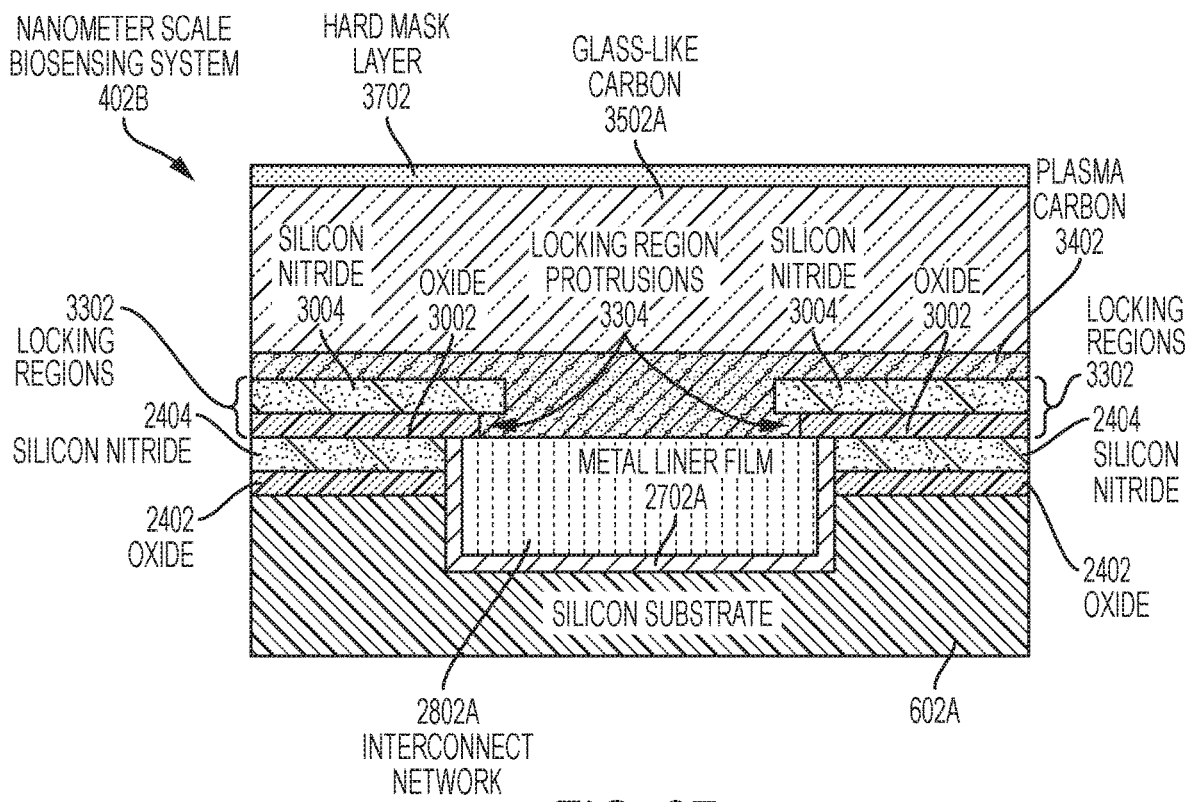
FIG. 37 depicts a cross-sectional view of the IC with a nanometer scale biosensor after a fabrication stage according to embodiments of the invention, wherein the biosensor system wiring is formed under the biosensor electrode according to embodiments of the invention.
Figure 38:
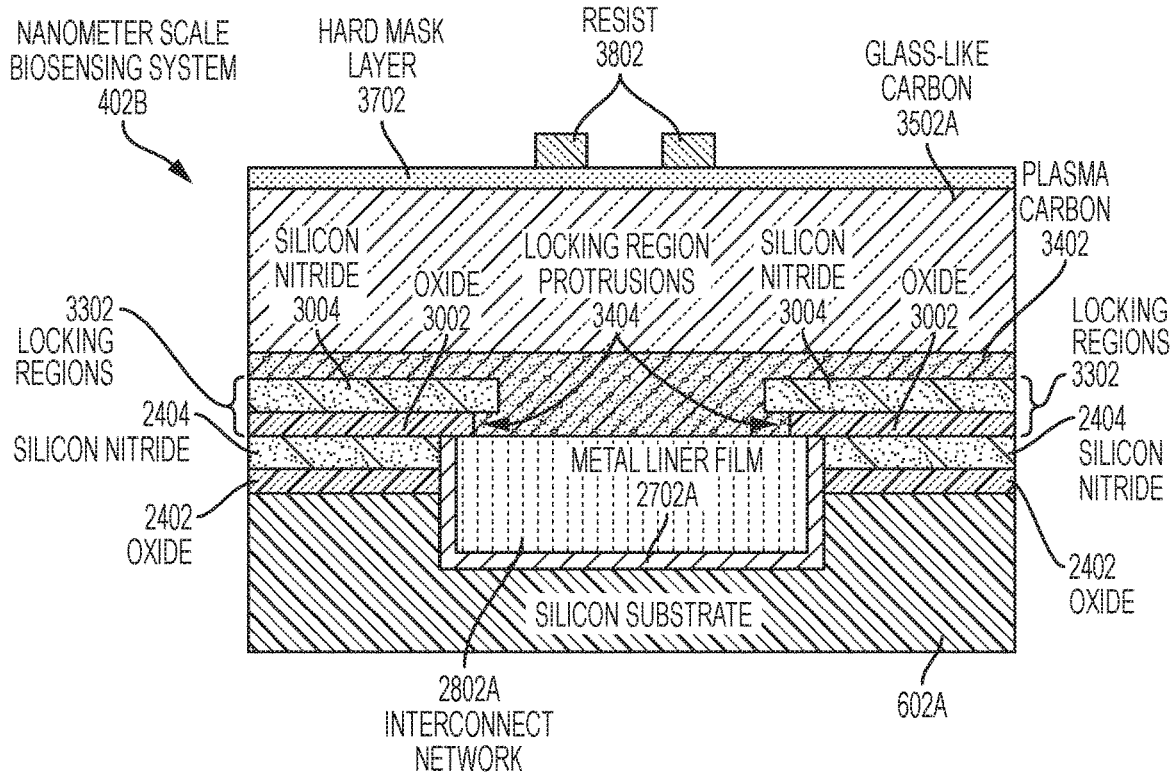
FIG. 38 depicts a cross-sectional view of the IC with a nanometer scale biosensor after a fabrication stage according to embodiments of the invention, wherein the biosensor system wiring is formed under the biosensor electrode according to embodiments of the invention.
Figure 39:
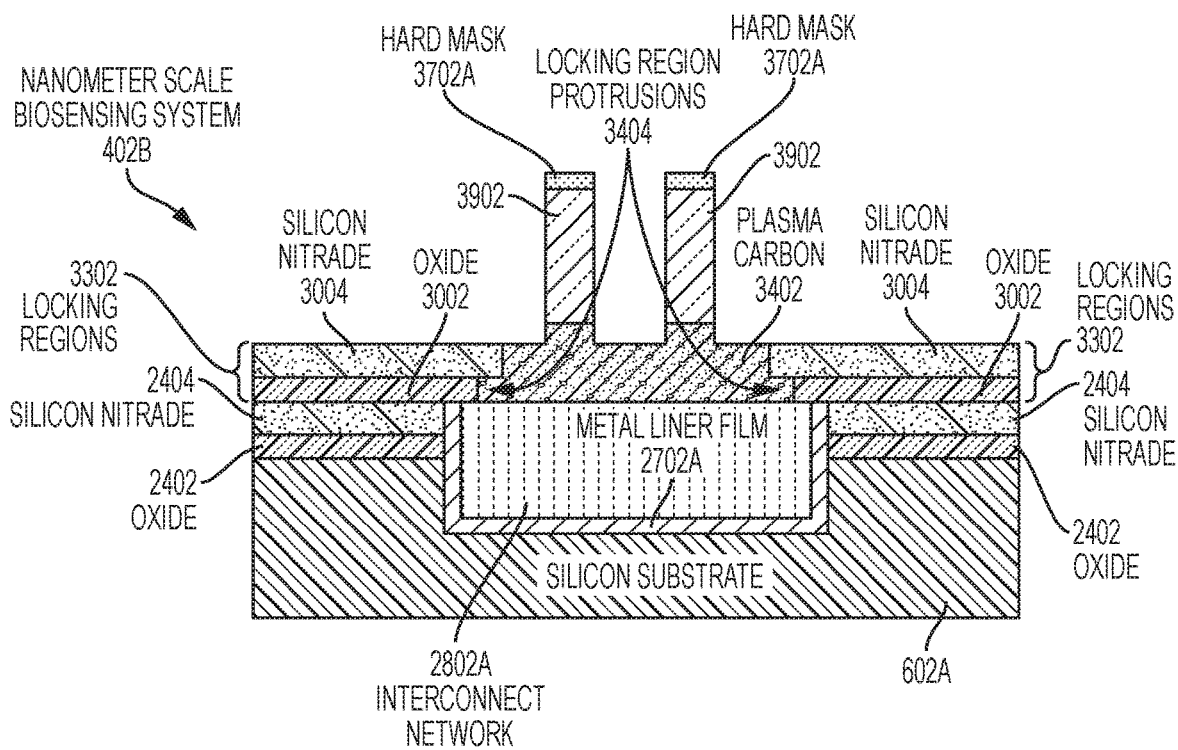
FIG. 39 depicts a cross-sectional view of the IC with a nanometer scale biosensor after a fabrication stage according to embodiments of the invention, wherein the biosensor system wiring is formed under the biosensor electrode according to embodiments of the invention.

In FIG. 37, a hard mask layer 3702 has been deposited, and in FIG. 38, a photo resist pattern 3802 for defining the pillars 3902 (shown in FIG. 39). In embodiments of the invention, the hard mask layer 3702 can be formed from titanium.

In FIG. 39, the glass-like carbon 3502A and the hard mask layer 3702 have been etched to form the hard masks 3702A and the glass-like carbon pillars 3902 in the glass-like carbon 3502A.

Figure 40:
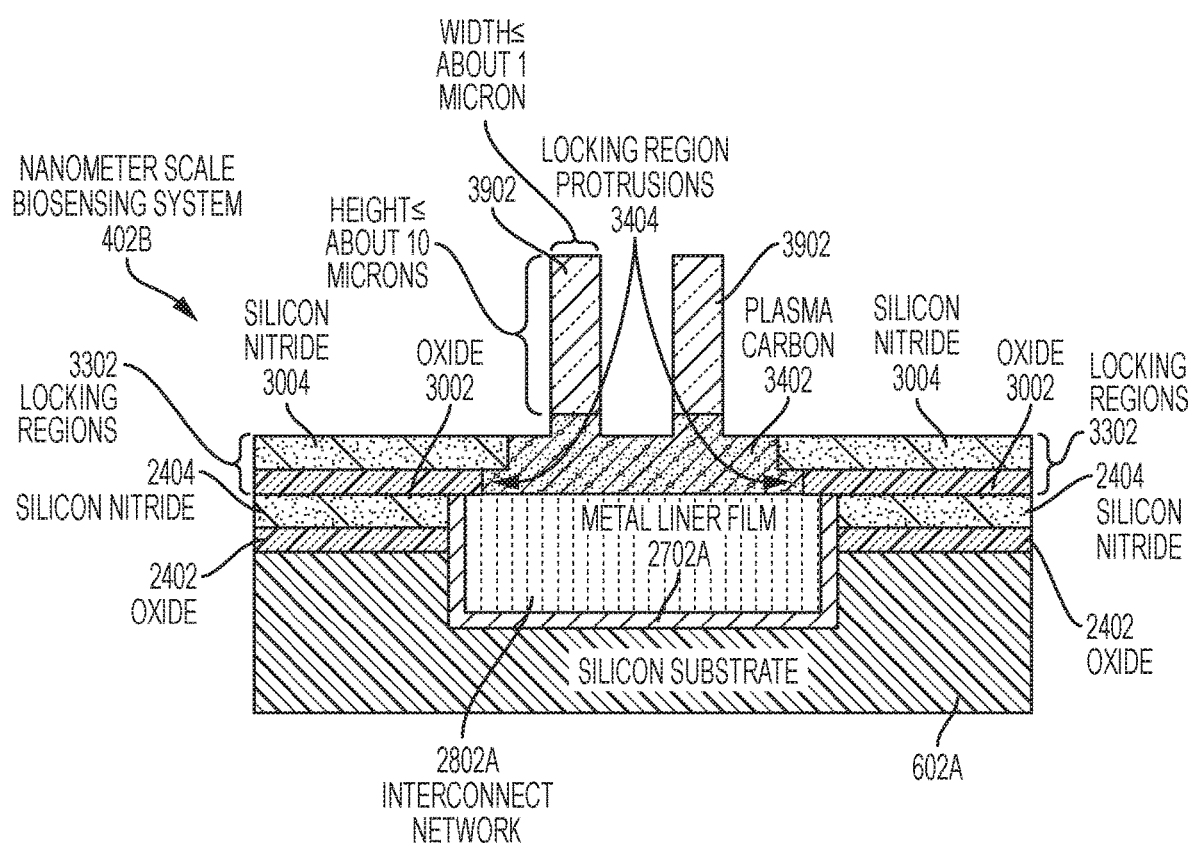
FIG. 40 depicts a cross-sectional view of the IC with a nanometer scale biosensor after a fabrication stage according to embodiments of the invention, wherein the biosensor system wiring is formed under the biosensor electrode according to embodiments of the invention.

In FIG. 40, the hard masks 3702A have been removed using conventional fabrication techniques (e.g., applying hydrogen peroxide or dilute hydrofluoric acid (DHF)). As depicted in FIG. 40, and in accordance with embodiments of the invention, each of the pillars 3902 has a height dimension that is less than about 10 microns and a width dimension that is less than about 1 micron.

The fabrication operations shown in FIGS. 17-23, with appropriate modifications where necessary based on the differences between biosensing system 402A and biosensing system 402B, can be applied after the operation shown in FIG. 40.

Figure 41:
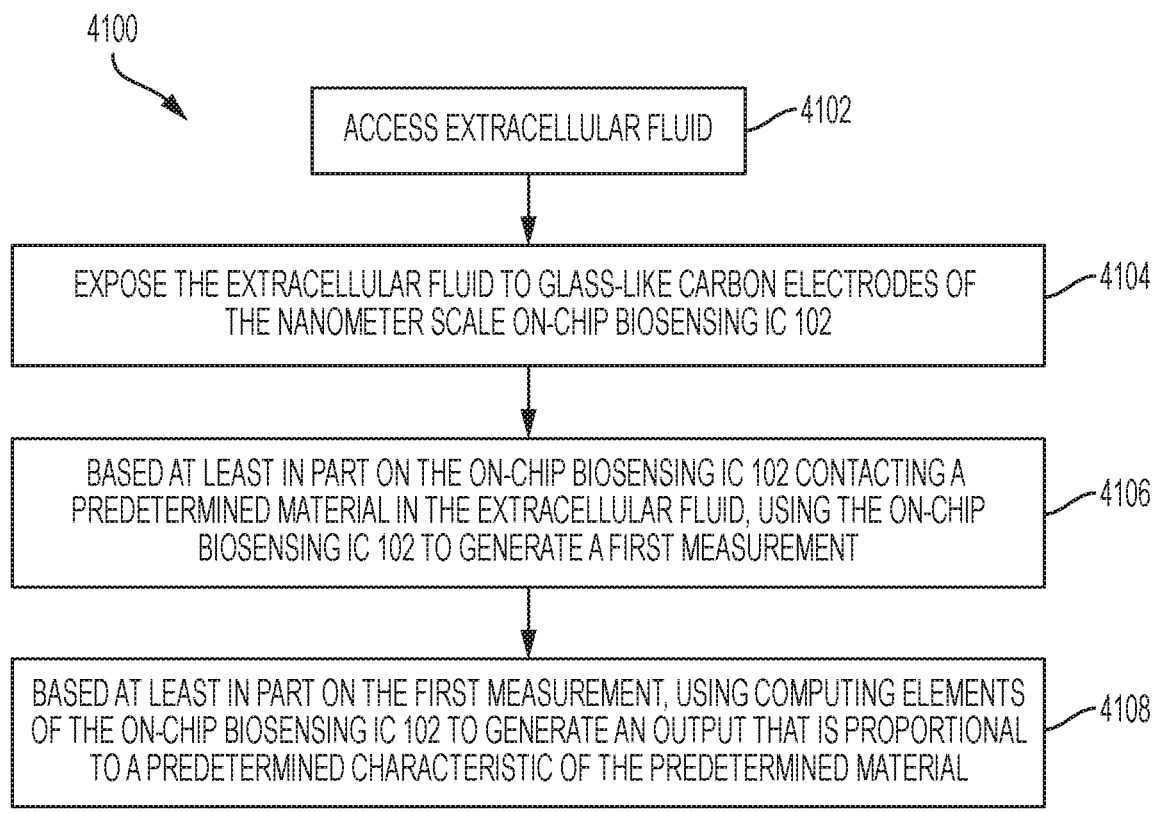
FIG. 41 depicts a flow diagram illustrating a method of using a biosensing IC having a nanometer scale biosensor according to embodiments of the invention.

FIG. 41 is a flow diagram illustrating a method 4100 for using the biosensing ICs 102, 102A, 102B according to one or more embodiments of the invention. Block 4102 accesses the extracellular fluid 104 (shown in FIG. 1). Block 4104 exposes extracellular fluid 104 to the nanometer scale glass-like carbon electrodes of the biosensing IC 102, 102A, 102B. In block 4106, based at least in part on the nanometer scale glass-like carbon electrodes of the biosensing IC 102, 102A, 102B contacting a predetermined material in the extracellular fluid 104, the biosensing IC 102, 102A, 102B generates a first measurement. In block 4108, based at least in part on the first measurement, a computer processor of the biosensing IC 102, 102A, 102B generates an output that is proportional to a predetermined characteristic of the predetermined material.

Although the present invention is primarily described in connection with use in human subjects, the teachings of the present invention can be used in organisms that include but are not limited to animals, reptiles and invertebrates. Additionally, the solution with the target analyte can be any aqueous environment or body of water, including oceans, lakes, streams and ponds.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

For purposes of the descriptions herein, the terms "upper," "lower," "right," "left," "vertical," "horizontal," "top," "bottom," and derivatives thereof shall relate to the described structures and methods, as oriented in the drawing figures. The terms "over," "overlying," "atop," "on top," "positioned on" or "positioned atop" mean that a first element, such as a first structure, is present on a second element, such as a second structure, where intervening elements such as an interface structure can be present between the first element and the second element. The phrase "direct contact" means that a first element, such as a first structure, and a second element, such as a second structure, are connected without any intermediary conducting, insulating or semiconductor layers at the interface of the two elements. The phrase "selective to," such as, for example, "a first element selective to a second element," means that a first element can be etched and the second element can act as an etch stop. The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

What is claimed is:

1. A biosensing integrated circuit (IC) apparatus comprising:
   a plurality of semiconductor substrate layers;
   a sensor element formed over a first one of the plurality of semiconductor substrate layers, wherein the sensor element is configured to, based at least in part on the sensor element interacting with a predetermined material, generate data representing a measureable electrical parameter; and
   an adhesion enhancement region configured to physically couple the sensor element to the first one of the plurality of semiconductor substrate layers;
   wherein the adhesion enhancement region comprises a protrusion configured to extend laterally with respect to a major surface of the first one of the plurality of semiconductor substrate layers; and
   wherein the protrusion is further configured to extend laterally into a groove formed in a locking region of the first one of the plurality of semiconductor substrate layers.

2. The apparatus of claim 1 further comprising an electrically conductive interconnect network configured to communicatively couple the data representing the measureable electrical parameter to computer elements formed on a second one of the plurality of semiconductor substrate layers.

3. The apparatus of claim 2 further comprising:
   a plurality of the sensor elements formed over the first one of the plurality of semiconductor substrate layers;
   wherein the sensor element comprises a first one of the plurality of sensor elements and is configured to, based at least in part on the first one of the plurality of sensor elements interacting with a first predetermined material, generate first data representing a first measureable electrical parameter;
   wherein a second one of the plurality of sensor elements is configured to, based at least in part on the second one of the plurality of sensor elements interacting with a second predetermined material, generate second data representing a second measureable electrical parameter;
   wherein the electrically conductive interconnect network and the computing elements are configured to couple the first data and the second data to the computing elements separately;
   wherein the computing elements are further configured to:
     associate the first data to the first one of the plurality of sensors and analyze the first data separately from the second data; and
     associate the second data to the second one of the plurality of sensors and analyze the second data separately from the first data.

4. The apparatus of claim 1 further comprising:
   an optical element formed on:
     the first one of the plurality of semiconductor substrate layers; or
     a second one of the plurality of semiconductor substrate layers;
     wherein the optical element is configured to, based at least in part on the optical element interacting optically with a predetermined material, generate data representing a measureable optical parameter.

5. The apparatus of claim 1, wherein:
   the sensor element comprises an electrode body;
   the electrode body comprises at least one pillar; and
   the at least one pillar comprises a glass-like carbon material.

6. The apparatus of claim 5, wherein the at least one pillar comprises:
   a height dimension comprising less than about 10 microns; and
   a width dimension comprising less than about 1 microns.

7. The apparatus of claim 5 wherein the sensor element further comprises a recognition enhancement element coupled to the at least one pillar and configured to, based at least in part on the recognition enhancement element interacting with the predetermined material, assist with generating the data representing the measureable electrical parameter.

* * * * *